United States Patent
Abe et al.

(10) Patent No.: US 11,597,745 B2
(45) Date of Patent: Mar. 7, 2023

(54) β-MODIFIED PHOSPHORIC ACID COMPOUND PRECURSOR, β-MODIFIED PHOSPHORIC ACID COMPOUND, REACTION INHIBITOR AND MEDICINE CONTAINING THE SAME, AND METHOD FOR INHIBITING REACTION

(71) Applicant: Japan Science and Technology Agency, Kawaguchi (JP)

(72) Inventors: Hiroshi Abe, Nagoya (JP); Yasuaki Kimura, Nagoya (JP)

(73) Assignee: Japan Science and Technology Agency, Kawaguchi (JP)

( * ) Notice: Subject to any disclaimer, the term of this patent is extended or adjusted under 35 U.S.C. 154(b) by 0 days.

(21) Appl. No.: 16/977,525

(22) PCT Filed: Mar. 8, 2019

(86) PCT No.: PCT/JP2019/009213
§ 371 (c)(1),
(2) Date: Oct. 23, 2020

(87) PCT Pub. No.: WO2019/172394
PCT Pub. Date: Sep. 12, 2019

(65) Prior Publication Data
US 2021/0284679 A1    Sep. 16, 2021

(30) Foreign Application Priority Data
Mar. 9, 2018 (JP) .............................. JP2018-043329

(51) Int. Cl.
*C07H 19/20* (2006.01)
*C07H 19/16* (2006.01)

(52) U.S. Cl.
CPC ............. *C07H 19/20* (2013.01); *C07H 19/16* (2013.01)

(58) Field of Classification Search
CPC ................................ C07H 19/16; C07H 19/20
See application file for complete search history.

(56) References Cited

U.S. PATENT DOCUMENTS

| | | | | |
|---|---|---|---|---|
| 7,592,446 B2* | 9/2009 | Huang | .................... | C07H 19/16 536/23.1 |
| 7,982,030 B2* | 7/2011 | Huang | .................... | C07H 19/20 536/27.21 |
| 8,354,524 B2* | 1/2013 | Huang | .................... | C07H 5/08 536/26.8 |
| 8,933,053 B2* | 1/2015 | McGuigan | ............... | A61P 35/02 514/51 |
| 9,109,001 B2* | 8/2015 | Parsy | ....................... | A61K 45/06 |
| 10,441,637 B2* | 10/2019 | Huang | ...................... | C12N 9/22 |
| 2013/0315868 A1 | 11/2013 | Mayes et al. | | |
| 2014/0057866 A1 | 2/2014 | McGuigan et al. | | |
| 2015/0157655 A1 | 6/2015 | Huang | | |
| 2016/0220595 A1 | 8/2016 | Liotta et al. | | |

FOREIGN PATENT DOCUMENTS

| | | |
|---|---|---|
| CN | 104540843 A | 4/2015 |
| CN | 105646629 A | 6/2016 |
| JP | H9136842 A | 5/1997 |
| WO | 8809796 A1 | 12/1988 |
| WO | 2012117246 A1 | 9/2012 |
| WO | 2014003950 A2 | 1/2014 |
| WO | 2014160484 A1 | 10/2014 |
| WO | 2015038596 A1 | 3/2015 |
| WO | 2016145102 A1 | 9/2016 |

OTHER PUBLICATIONS

Brachwitz, DE 19750508 A1, 1999, machine translation. (Year: 1999).*
Antonov et al., "Complexes of Ribonuclease A with 2'-Deoxy-2'-Fluororibose Substrate Analogues Studied by Nuclear Magnetic Resonance", Eur. J. Biochem., 1978, pp. 45-54, vol. 87.
Bergmann et al., "Organic Fluorine Compounds Fluorine Derivatives of Mevalolactone", Tetrahedron Letters, 1960, pp. 20-22, No. 8.
Dantzman et al., "Reactivity of a 2'-Thio Nucleotide Analog", J. Am. Chem. Soc., 1996, pp. 11715-11719, vol. 118, No. 47.
Ikehara et al., "Studies on Nucleosides and Nucleotides. LXXXVIII. Sythesis of a Non-hydrolyzable Substrate Analog of Rihonuclease TI, 2'-Deoxy-2'-fluoroguanylyl-(3'-5')-uridine", Chem. Pharm. Bull., 1981, pp. 2408-2412, vol. 29, No. 9.
Lee et al., "The Enzymatic Hydrolysis of the Phosphate Ester Bond in Some Thionucleotides", Biochemica et Biophysica Acta, 1979, pp. 223-231, vol. 561.

(Continued)

*Primary Examiner* — Layla D Berry
(74) *Attorney, Agent, or Firm* — The Webb Law Firm

(57) ABSTRACT

A β-modified phosphoric acid compound precursor that inhibits the progress of a phosphorylation reaction having a partial structure represented by

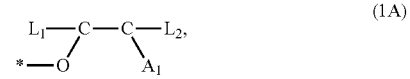

(1A)

where $A_1$ represents —$SR_1$, —S—S—$R_1$, —$SeR_1$, or —X, where X is a halogen selected from fluoro, chloro, bromo, and iodo; $R_1$ represents hydrogen, an alkyl group having 1 to 20 carbon atoms, or the like; $L_1$ represents hydrogen, an alkyl group having 1 to 20 carbon atoms, or the like; $L_2$ represents an alkyl group having 1 to 20 carbon atoms, or the like; $L_1$ and $L_2$ may be linked to each other to form a 4 to 6-membered ring structure; $L_1$ and $L_2$ may each have a substituent; and the symbol * represents a bond to be bonded to a phosphate group by phosphorylation. Further, provided are a reaction inhibitor and a medicine, each of which includes the β-modified phosphoric acid compound precursor.

12 Claims, 5 Drawing Sheets
Specification includes a Sequence Listing.

(56) References Cited

OTHER PUBLICATIONS

Patel et al., "Synthesis and Properties of 2'-Deoxy-2'-thiocytidine", J. Org. Chem., 1980, pp. 4830-4834, vol. 45, No. 24.

Puffer et al., "2'-Methylseleno-modified Oligoribonucleotides for X-ray Crystallography Synthesized by ACE RNA Solid-phase Approach", Nucleaic Acids Research, 2008, pp. 970-983, vol. 36, No. 3.

Salon et al., "Sythesis and Crystal Structure of 2'-Se-Modified Guanosine Containing DNA", J. Org. Chem., 2010, pp. 637-641, vol. 75, No. 3.

Santner et al., "The Synthesis of 2'-methylseleno Adenosine and Guanosine 5'-triphosphates", Bioorganic & Medicinal Chemistry, 2012, pp. 2416-2418, vol. 20.

Shokar et al., "S-Adenosylhomocysteine Hydrolase of the Protozoan Parasite Trichomonas Vaginalis: Potent Inhibitory Activity of 9-(2-deoxy-2-fluoro-B.D-arabinofuranosyl)adenine", Bioorganic & Medicinal Chemistry Letters, 2012, pp. 4203-4205, vol. 22.

Uesugi et al., "Synthesis and Properties of ApU Analogues Containing 2'-Halo-2'-deoxyadenosines. Effects of 2' Substituents on Oligonucleotide Conformation", Biochemistry, 1982, pp. 5870-5877, vol. 21, No. 23.

Uesugi et al., "Synthesis and Characterization of the Dinucleoside Monophosphates Containing 2'-Fluoro-2'-deoxyadenosine", Biochemistry, 1981, pp. 3056-3062, vol. 20, No. 11.

Wnuk et al., "Synthesis and Cytotoxicity of 9-(2-deoxy-2-alkyldithio-B-D-arabino-furanosyl)purine nucleosides which are Stable Precursors to Potential Mechanistic Probes of Ribonucleotide Reductases", The Royal Society of Chemistry, Nov. 20, 2003, 7 pages.

"Partial Supplementary European Search Report", dated Sep. 3, 2021.

Dziewiszek et al., "Derivatives of 1-(2-Deoxy-2-fluoro-B-D-arabinofuranosyl)-5-phenyluracil and 5-Benzyluracil. Synthesis and Biological Properties", Nucleosides, Nucleotides & Nucleic Acids, 1994, pp. 77-94, vol. 13, No. 1-3.

Kukhanova et al., "Inhibitory Analysis of DNA Polymerases from Human Viruses using Modified Substrates", Molekulyarnaya Viologiya, 1994, pp. 530-541, vol. 28, No. 3, English-language Abstract.

Semizarov et al., "Modified Nucleoside 5'-triphosphates Containing 2',3'-fused Three-membered Rings as Substrates for Different DNA Polymerases", FEBS Letters, Jul. 1993, pp. 45-48, vol. 327, No. 1.

"Extended European Search Report" for related Application No. EP 19763431.4, dated Dec. 9, 2021.

* cited by examiner

[Fig. 1]
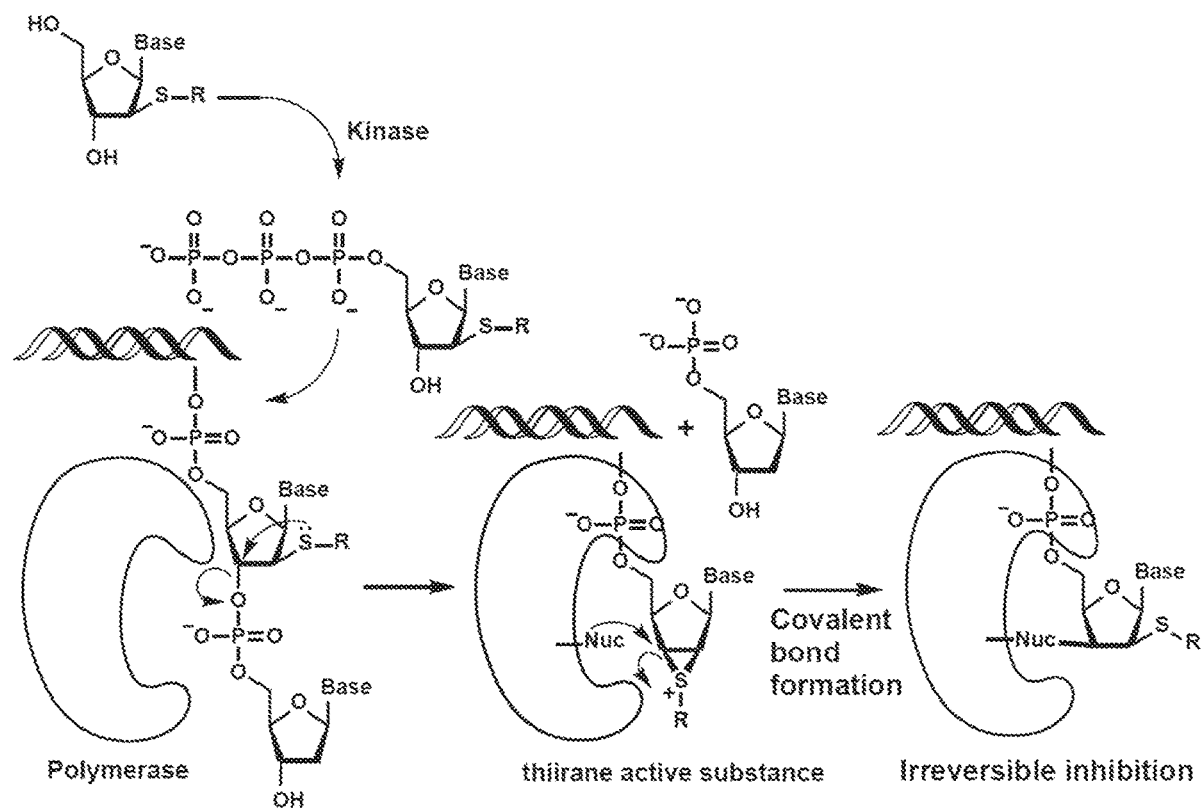

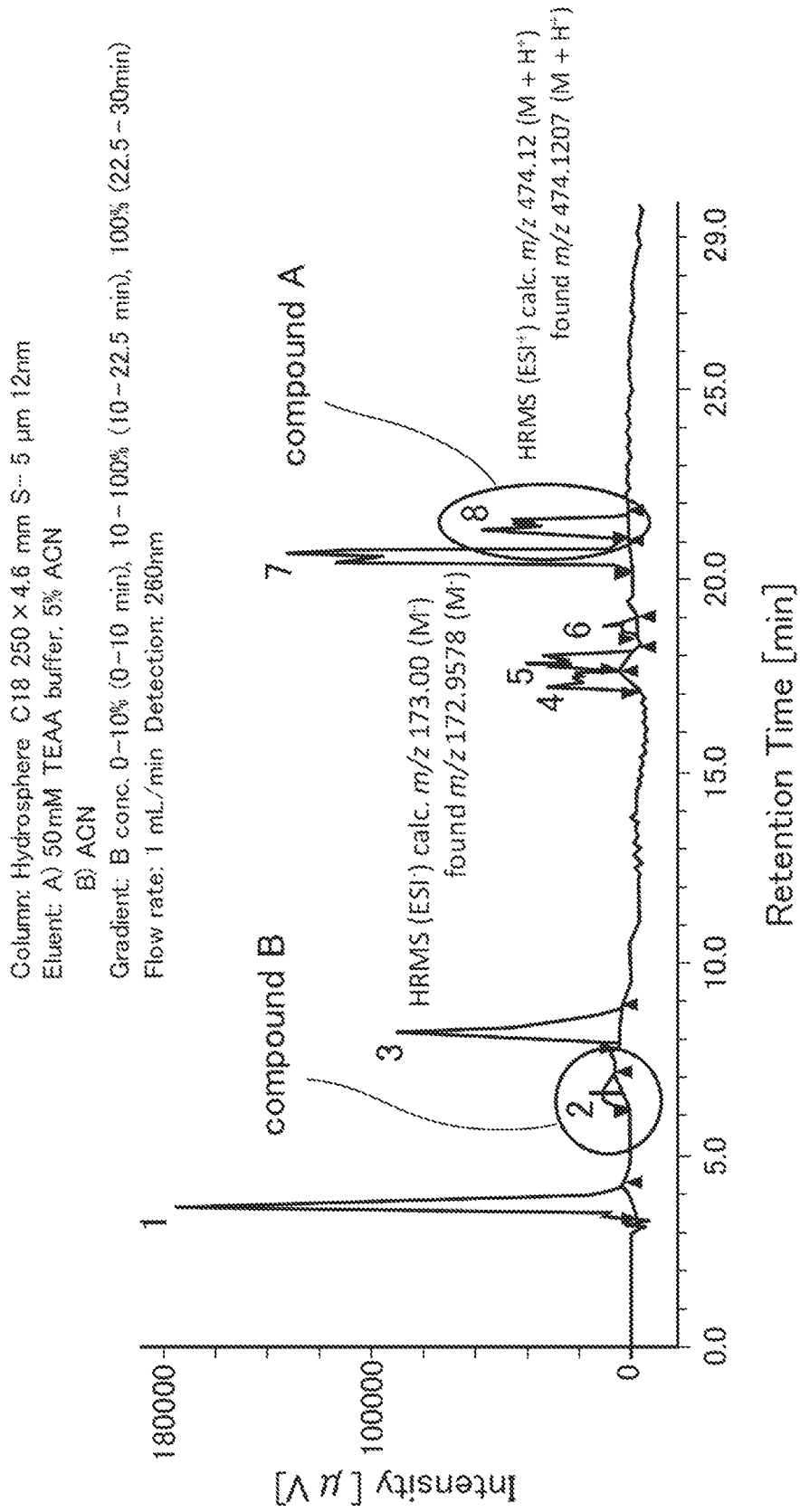
[Fig. 2]

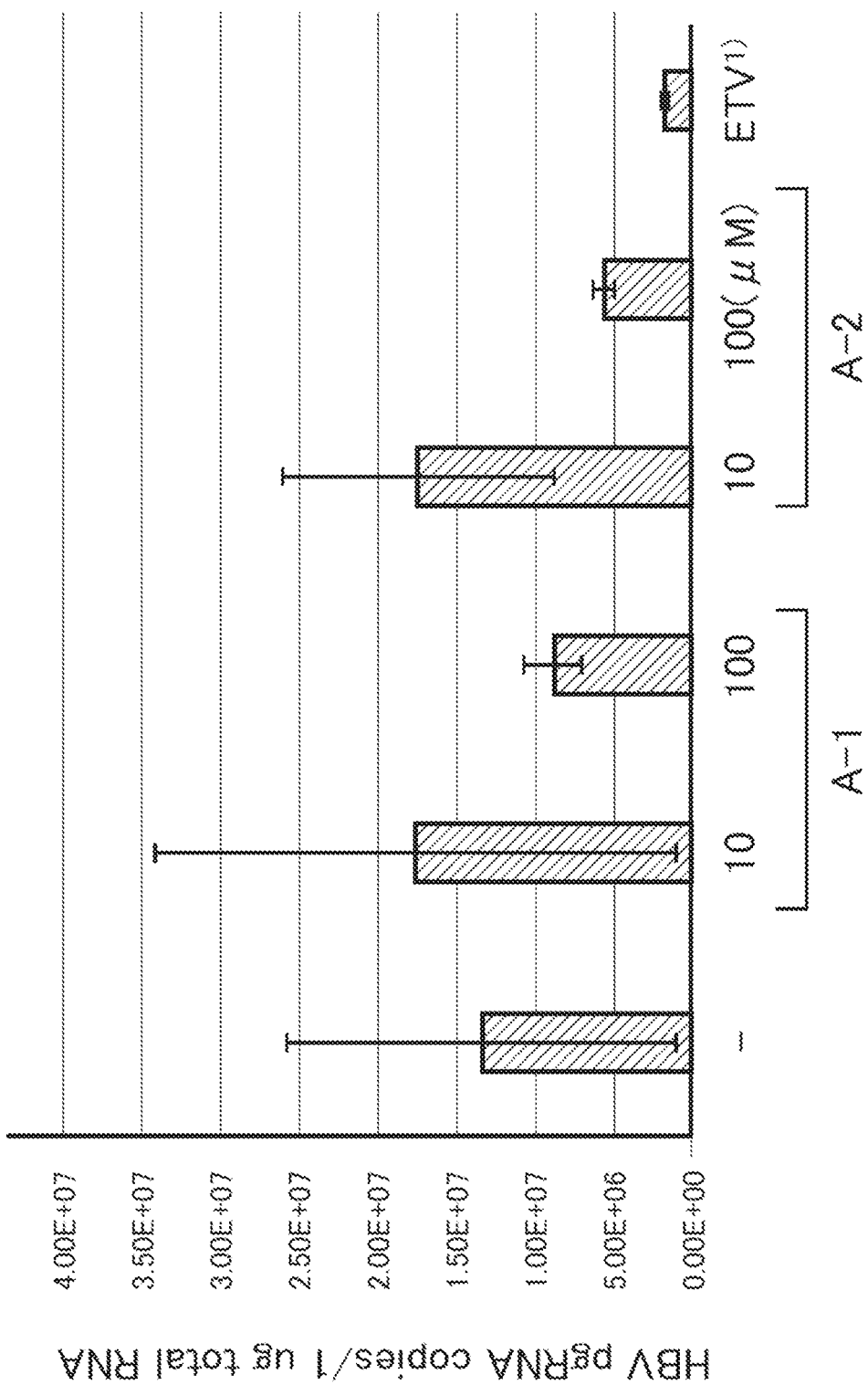
[Fig. 3]

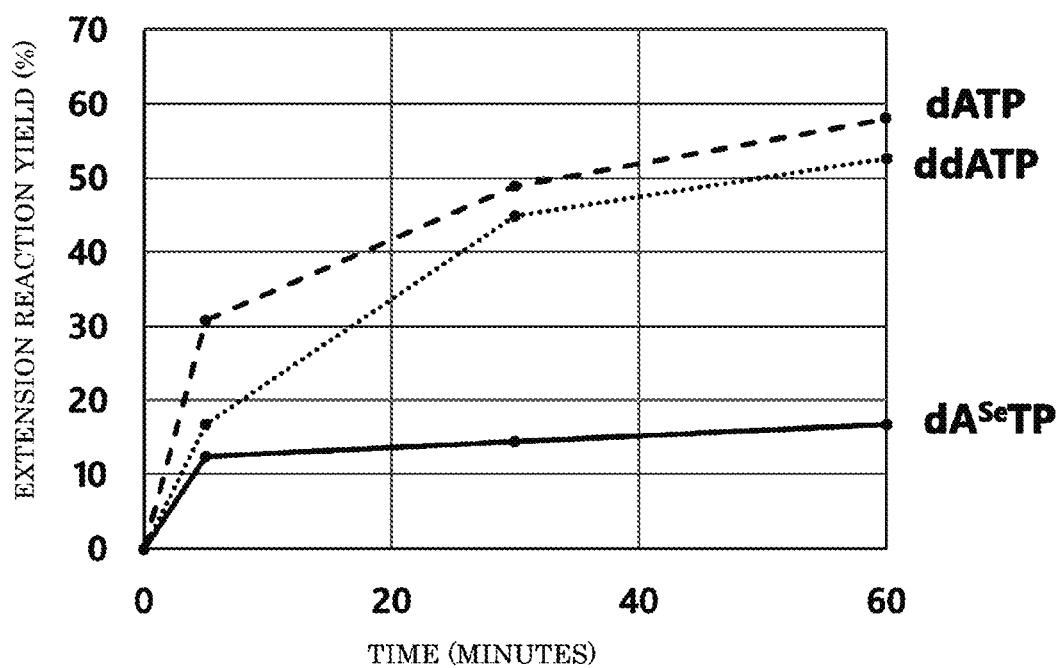
[FIG. 4]

[FIG. 5]
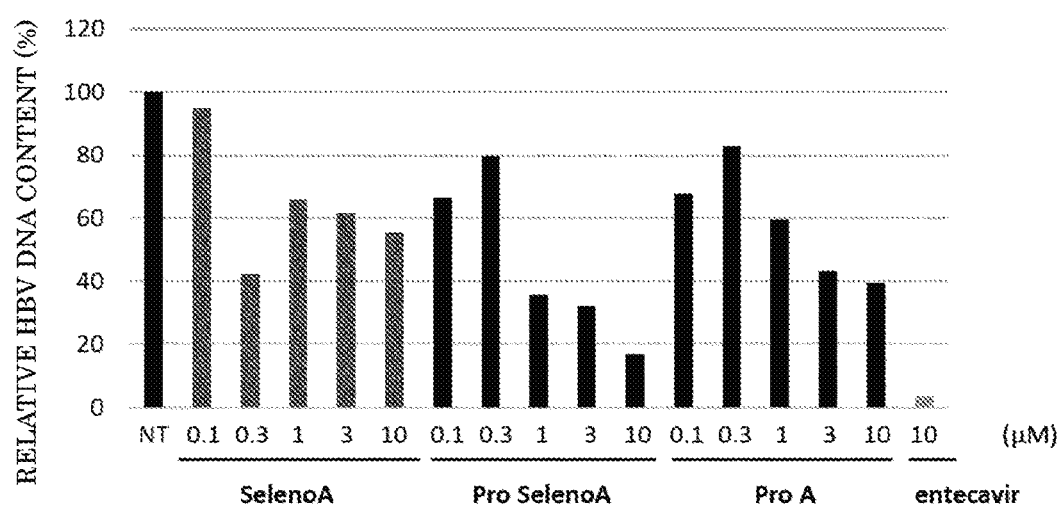

β-MODIFIED PHOSPHORIC ACID COMPOUND PRECURSOR, β-MODIFIED PHOSPHORIC ACID COMPOUND, REACTION INHIBITOR AND MEDICINE CONTAINING THE SAME, AND METHOD FOR INHIBITING REACTION

CROSS-REFERENCE TO RELATED APPLICATIONS

This application is the United States national phase of International Application No. PCT/JP2019/009213 filed Mar. 8, 2019, and claims priority to Japanese Patent Application No. 2018-043329 filed Mar. 9, 2018, the disclosures of which are hereby incorporated by reference in their entirety.

REFERENCE TO A SEQUENCE LISTING SUBMITTED VIA EFS-WEB

The Sequence Listing associated with this application is filed in electronic format via EFS-Web and is hereby incorporated by reference into the specification in its entirety. The name of the text file containing the Sequence Listing is 2004827_ST25.txt. The size of the text file is 898 bytes, and the text file was created on Dec. 8, 2021.

BACKGROUND OF THE INVENTION

Technical Field

The present invention relates to a β-modified phosphoric acid compound precursor, a β-modified phosphoric acid compound, a reaction inhibitor, a medicine containing the reaction inhibitor, and a method for inhibiting a reaction, and particularly relates to a β-modified phosphoric acid compound precursor that inhibits progress of a reaction after phosphorylation in a reaction involving the phosphorylation, a β-modified phosphoric acid compound, a reaction inhibitor, a medicine containing the reaction inhibitor, and a method for inhibiting a reaction.

Background Art

Phosphorylation is an important process in a biological reaction, and various reactions involving phosphorylation are performed in vivo. For example, in replication of DNA, a DNA polymerase performs a reaction involving phosphorylation of DNA. By using a primer sequence as a starting point and single-stranded DNA as a template, the DNA polymerase sequentially binds the deoxynucleotide triphosphate (dNTP) complementary to the single-stranded DNA onto the 3'-end side to extend the complementary strand DNA in a 3'→5' direction. In this reaction, two phosphate groups of the triphosphate of dNTP are dephosphorylated by a DNA polymerase, and the remaining one phosphate group binds to a hydroxyl group at the 3-position of sugar (deoxyribose) on the 3'-end side. As a result, the sugar on the 3'-end side is phosphorylated, and the complementary strand DNA is extended. The polymerase is involved in DNA replication and transcription, and is also an important target protein in therapeutic agents for a cancer, and a disease caused by viruses or the like.

Further, mevalonic acid is a compound involved in the synthesis of terpenoids or steroids. The mevalonic acid is phosphorylated by a mevalonate kinase using ATP as a substrate and is changed to 5-phosphomevalonic acid, and the 5-phosphomevalonic acid is converted into cholesterol or the like by the subsequent processes. The mevalonic acid is also known as an important target substance in therapeutic agents for hyperlipidemia and the like.

As described above, phosphorylation is an important process in a biological reaction, and has the potential to provide a method for treating various diseases if the subsequent reaction can be specifically and efficiently inhibited. However, the conventional technique is insufficient to selectively and efficiently inhibit the biological reaction caused by the phosphorylation.

For example, Japanese Patent Application Publication No. JP H09-136842 discloses acyclovir as an inhibitor of a DNA polymerase. Acyclovir undergoes monophosphorylation in a virus and triphosphorylation in a host (human), binds onto the 3'-end side of the extending chain in a DNA polymerase reaction, and competitively inhibits the viral DNA polymerase.

SUMMARY OF INVENTION

However, a compound such as acyclovir only inhibits the extension of DNA, and there has been a demand for an inhibitor that inhibits the reaction more efficiently and strongly.

It is an object of the present invention to provide a β-modified phosphoric acid compound precursor that can specifically inhibit progress of a reaction after phosphorylation in a reaction involving the phosphorylation, a β-modified phosphoric acid compound, a reaction inhibitor, a medicine containing the reaction inhibitor, and a method for inhibiting a reaction.

The present inventors have conducted the intensive studies to solve the problem described above. As a result, with regard to a compound having a partial structure in which a hydroxyl group is bonded to one carbon (α-position) and a specific modifying group is bonded to the other carbon (β-position) of a carbon-carbon bond, it has been found that an active species having high reactivity is generated due to the phosphorylation of the hydroxyl group. Further, the present inventors have found that the reaction by a biomolecule after the phosphorylation is specifically inhibited by the active species, and thus have completed the present invention.

That is, the present invention is a β-modified phosphoric acid compound precursor to be phosphorylated by phosphorylation, including a partial structure represented by the following formula 1A in the molecule thereof,
[Chemical Formula 1]

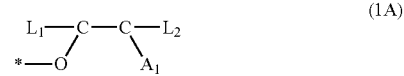

(1A)

in which $A_1$ represents —$SR_1$, —S—S—$R_1$, —$SeR_1$, or —X (where X means a halogen selected from fluoro, chloro, bromo, and iodo), $R_1$ represents hydrogen, an alkyl group having 1 to 20 carbon atoms, an aryl group having 1 to 20 carbon atoms, or an alkenyl group having 1 to 20 carbon atoms, $L_1$ represents hydrogen, an alkyl group having 1 to 20 carbon atoms, an aryl group having 1 to 20 carbon atoms, or an alkenyl group having 1 to 20 carbon atoms, $L_2$ represents an alkyl group having 1 to 20 carbon atoms, an aryl group having 1 to 20 carbon atoms, or an alkenyl group having 1 to 20 carbon atoms, $L_1$ and $L_2$ may be linked to each other to form a 4 to 6-membered ring structure, the ring structure includes one or more kinds of elements selected from carbon, nitrogen, oxygen, and sulfur, $L_1$ and $L_2$ may each have 1 or 2 or more substituents selected from a hydroxyl group, a carboxyl group, an amino group, an alkyl group, an aryl group, a phospholipid containing one or more saturated and/or unsaturated fatty acids each having 15 to 30 carbon atoms, a monophosphate group, diphosphate group, or triphosphate group, and a base (where the base means adeninyl, guaninyl, cytosinyl, thyminyl, uracilyl, N-methyladeninyl, N-benzoyladeninyl, 2-methylthioadeninyl, 2-aminoadeninyl, 7-methylguaninyl, N-isobutyrylguaninyl, 5-fluorocytosinyl, 5-bromocytosinyl, 5-methylcytosinyl, 4-N-methylcytosinyl, 4-N,N-dimethylcytosinyl, 5-fluorouracilyl, 5-bromouracilyl, 5-chlorouracilyl, or 5,6-dihydrouracilyl), and the symbol * represents a bond to be bonded to a phosphate group by phosphorylation, and means bonding of hydrogen or a substituent other than a phosphate group before the phosphorylation.

In this case, it is preferred that the β-modified phosphoric acid compound precursor is a nucleoside derivative represented by the following formula 2A, or a nucleic acid having the nucleoside derivative at the 3'-end thereof,

[Chemical Formula 2]

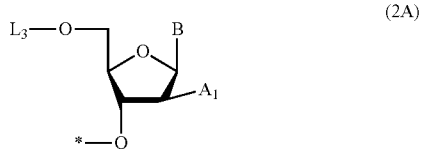

(2A)

in which $A_1$ represents —$SR_1$, —S—S—$R_1$, —$SeR_1$, or —X (where X means a halogen selected from fluoro, chloro, bromo, and iodo), $R_1$ represents hydrogen, an alkyl group having 1 to 20 carbon atoms, an aryl group having 1 to 20 carbon atoms, or an alkenyl group having 1 to 20 carbon atoms, $L_3$ represents hydrogen, or a monophosphate group, diphosphate group, or triphosphate group represented by the following formula 2D,

[Chemical Formula 3]

(2D)

(where n is an integer of 1 to 3, $Z_1$ represents a hydroxyl group, or a methyl ester, ethyl ester, isopropyl ester, n-butyl ester, benzyl ester, or phenyl ester of glycine, alanine, valine, leucine, phenylalanine, tryptophan, methionine, or proline, $Z_2$ represents hydrogen, an alkyl group having 1 to 4 carbon atoms, a halogen, or a phenyl group, and $Z_1$s may be the same as or different from each other in a case where n is 2 or more), B represents a base selected from adeninyl, guaninyl, cytosinyl, thyminyl, uracilyl, N-methyladeninyl, N-benzoyladeninyl, 2-methylthioadeninyl, 2-aminoadeninyl, 7-methylguaninyl, N-isobutyrylguaninyl, 5-fluorocytosinyl, 5-bromocytosinyl, 5-methylcytosinyl, 4-N-methylcytosinyl, 4-N,N-dimethylcytosinyl, 5-fluorouracilyl, 5-bromouracilyl, 5-chlorouracilyl, or 5,6-dihydrouracilyl, and the symbol * represents a bond to be bonded to a phosphate group by phosphorylation, and means bonding of hydrogen or a substituent other than a phosphate group before the phosphorylation.

Alternatively, in the above case, it is preferred that the β-modified phosphoric acid compound precursor is a mevalonic acid derivative represented by the following formula 3A,

[Chemical Formula 4]

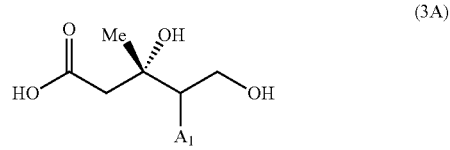

(3A)

in which $A_1$ represents —$SR_1$, —S—S—$R_1$, —$SeR_1$, or —X (where X means a halogen selected from fluoro, chloro, bromo, and iodo), and $R_1$ represents hydrogen, an alkyl group having 1 to 20 carbon atoms, an aryl group having 1 to 20 carbon atoms, or an alkenyl group having 1 to 20 carbon atoms.

Alternatively, further, in the above case, the β-modified phosphoric acid compound precursor according to claim 1, in which the β-modified phosphoric acid compound precursor is a phosphatidylinositol derivative represented by the following formula 4A,

[Chemical Formula 5]

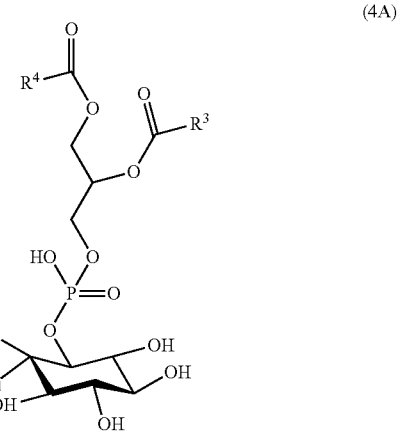

(4A)

in which $A_1$ represents —$SR_1$, —S—S—$R_1$, —$SeR_1$, or —X (where X means a halogen selected from fluoro, chloro, bromo, and iodo), $R_1$ represents hydrogen, an alkyl group having 1 to 20 carbon atoms, an aryl group having 1 to 20 carbon atoms, or an alkenyl group having 1 to 20 carbon atoms, $R_3$ is an unsaturated fatty acid selected from arachidonic acid, linoleic acid, and linolenic acid, and $R_4$ is a saturated fatty acid selected from stearic acid, and palmitic acid.

The present invention is a β-modified phosphoric acid compound, including a partial structure represented by the following formula 1B in the molecule thereof,

[Chemical Formula 6]

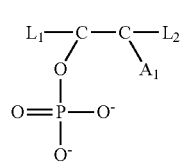

(1B)

in which $A_1$ represents —$SR_1$, —S—S—$R_1$, —$SeR_1$, or —X (where X means a halogen selected from fluoro, chloro, bromo, and iodo), $R_1$ is selected from hydrogen, an alkyl group having 1 to 20 carbon atoms, an aryl group having 1 to 20 carbon atoms, and an alkenyl group having 1 to 20 carbon atoms, $L_1$ represents hydrogen, an alkyl group having 1 to 20 carbon atoms, an aryl group having 1 to 20 carbon atoms, or an alkenyl group having 1 to 20 carbon atoms, $L_2$ represents an alkyl group having 1 to 20 carbon atoms, an aryl group having 1 to 20 carbon atoms, or an alkenyl group having 1 to 20 carbon atoms, $L_1$ and $L_2$ may be linked to each other to form a 4 to 6-membered ring structure, the ring structure includes one or more kinds of elements selected from carbon, nitrogen, oxygen, and sulfur, and $L_1$ and $L_2$ may each have 1 or 2 or more substituents selected from a hydroxyl group, a carboxyl group, an amino group, an alkyl group, an aryl group, a phospholipid containing one or more saturated and/or unsaturated fatty acids each having 15 to 30 carbon atoms, a monophosphate group, diphosphate group, or triphosphate group, and a base (where the base means adeninyl, guaninyl, cytosinyl, thyminyl, uracilyl, N-methyladeninyl, N-benzoyladeninyl, 2-methylthioadeninyl, 2-aminoadeninyl, 7-methylguaninyl, N-isobutyrylguaninyl, 5-fluorocytosinyl, 5-bromocytosinyl, 5-methylcytosinyl, 4-N-methylcytosinyl, 4-N,N-dimethylcytosinyl, 5-fluorouracilyl, 5-bromouracilyl, 5-chlorouracilyl, or 5,6-dihydrouracilyl).

In this case, it is preferred that the β-modified phosphoric acid compound is a nucleoside derivative represented by the following formula 2B or a nucleic acid having the nucleoside derivative at the 3'-end thereof,

[Chemical Formula 7]

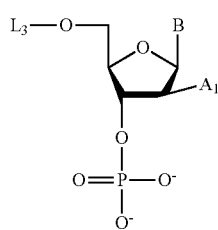

(2B)

in which $A_1$ represents —$SR_1$, —S—S—$R_1$, —$SeR_1$, or —X (where X means a halogen selected from fluoro, chloro, bromo, and iodo), $R_1$ represents hydrogen, an alkyl group having 1 to 20 carbon atoms, an aryl group having 1 to 20 carbon atoms, or an alkenyl group having 1 to 20 carbon atoms, $L_3$ represents hydrogen, or a monophosphate group, diphosphate group, or triphosphate group represented by the following formula 2D,

[Chemical Formula 8]

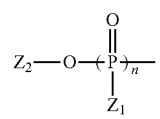

(2D)

(where n is an integer of 1 to 3, $Z_1$ represents a hydroxyl group, or a methyl ester, ethyl ester, isopropyl ester, n-butyl ester, benzyl ester, or phenyl ester of glycine, alanine, valine, leucine, phenylalanine, tryptophan, methionine, or proline, $Z_2$ represents hydrogen, an alkyl group having 1 to 4 carbon atoms, a halogen, or a phenyl group, and $Z_{1s}$ may be the same as or different from each other in a case where n is 2 or more), and B represents a base selected from adeninyl, guaninyl, cytosinyl, thyminyl, uracilyl, N-methyladeninyl, N-benzoyladeninyl, 2-methylthioadeninyl, 2-aminoadeninyl, 7-methylguaninyl, N-isobutyrylguaninyl, 5-fluorocytosinyl, 5-bromocytosinyl, 5-methylcytosinyl, 4-N-methylcytosinyl, 4-N, N-dimethylcytosinyl, 5-fluorouracilyl, 5-bromouracilyl, 5-chlorouracilyl, or 5,6-dihydrouracilyl.

The present invention is a reaction inhibitor for inhibiting progress of a reaction after phosphorylation in a reaction involving the phosphorylation, including the β-modified phosphoric acid compound precursor described in any one of the above items.

In this case, it is preferred that the β-modified phosphoric acid compound precursor is a nucleoside derivative represented by the above formula 2A or a nucleic acid having the nucleoside derivative at the 3'-end thereof, and inhibits a reaction of a DNA polymerase.

Further, the present invention is a medicine, including the reaction inhibitor described above.

The present invention is a method for inhibiting a reaction, for inhibiting progress of a reaction after phosphorylation in a reaction involving the phosphorylation by the reaction inhibitor described in any one of the above items, including: a step of preparing a β-modified phosphoric acid compound precursor represented by the above formula 1A; and a step of generating a β-modified phosphoric acid compound represented by the above formula 1B by phosphorylating the β-modified phosphoric acid compound precursor, and generating an active species represented by the following formula 1C by partially cleaving the β-modified phosphoric acid compound,

[Chemical Formula 9]

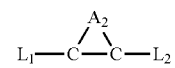

(1C)

in which $A_2$ represents —S—, —$S^+(R_1)$—, —$S^+(S-R_1)$—, —$Se^+(R_1)$—, or —$X^+$— (where X means a halogen selected from fluoro, chloro, bromo, and iodo), $R_1$ represents hydrogen, an alkyl group having 1 to 20 carbon atoms, an aryl group having 1 to 20 carbon atoms, or an alkenyl group having 1 to 20 carbon atoms, $L_1$ represents hydrogen, an alkyl group having 1 to 20 carbon atoms, an aryl group having 1 to 20 carbon atoms, or an alkenyl group having 1 to 20 carbon atoms, $L_2$ represents an alkyl group having 1 to 20 carbon atoms, an aryl group having 1 to 20 carbon atoms, or an alkenyl group having 1 to 20 carbon atoms, $L_1$ and $L_2$ may be linked to each other to form a 4 to 6-membered ring structure, the ring structure includes one or more kinds of elements selected from carbon, nitrogen, oxygen, and sulfur, and $L_1$ and $L_2$ may each have 1 or 2 or more substituents selected from a hydroxyl group, a carboxyl group, an amino group, an alkyl group, an aryl group, a phospholipid containing one or more saturated and/or unsaturated fatty acids each having 15 to 30 carbon atoms, a monophosphate group, diphosphate group, or triphosphate group, and a base (where the base means adeninyl, guaninyl, cytosinyl, thyminyl, uracilyl, N-methyladeninyl, N-benzoyladeninyl, 2-methylthioadeninyl, 2-aminoadeninyl, 7-methylguaninyl, N-isobutyrylguaninyl, 5-fluorocytosinyl, 5-bromocytosinyl, 5-methylcytosinyl, 4-N-methylcytosinyl, 4-N,N-dimethylcytosinyl, 5-fluorouracilyl, 5-bromouracilyl, 5-chlorouracilyl, or 5,6-dihydrouracilyl).

In this case, it is preferred that the β-modified phosphoric acid compound precursor is a compound represented by the above formula 2A, the β-modified phosphoric acid compound is a compound represented by the above formula 2B, and the active species is a compound represented by the following formula 2C, [Chemical Formula 10]

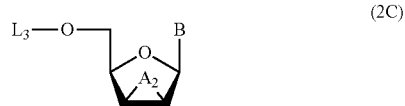

(2C)

in which $A_2$ represents —S—, —S$^+$($R_1$)—, —S$^+$(S—$R_1$)—, —Se$^+$($R_1$)—, or —X$^+$— (where X means a halogen selected from fluoro, chloro, bromo, and iodo), $R_1$ represents hydrogen, an alkyl group having 1 to 20 carbon atoms, an aryl group having 1 to 20 carbon atoms, or an alkenyl group having 1 to 20 carbon atoms, $L_3$ represents hydrogen, or a monophosphate group, diphosphate group, or triphosphate group represented by the following formula 2D, [Chemical Formula 11]

(2D)

(where n is an integer of 1 to 3, $Z_1$ represents a hydroxyl group, or a methyl ester, ethyl ester, isopropyl ester, n-butyl ester, benzyl ester, or phenyl ester of glycine, alanine, valine, leucine, phenylalanine, tryptophan, methionine, or proline, $Z_2$ represents hydrogen, an alkyl group having 1 to 4 carbon atoms, a halogen, or a phenyl group, and $Z_1$s may be the same as or different from each other in a case where n is 2 or more), and B represents a base selected from adeninyl, guaninyl, cytosinyl, thyminyl, uracilyl, N-methyladeninyl, N-benzoyladeninyl, 2-methylthioadeninyl, 2-aminoadeninyl, 7-methylguaninyl, N-isobutyrylguaninyl, 5-fluorocytosinyl, 5-bromocytosinyl, 5-methylcytosinyl, 4-N-methylcytosinyl, 4-N,N-dimethylcytosinyl, 5-fluorouracilyl, 5-bromouracilyl, 5-chlorouracilyl, or 5,6-dihydrouracilyl.

According to the present invention, a β-modified phosphoric acid compound precursor that can specifically inhibit progress of a reaction after phosphorylation in a reaction involving the phosphorylation by an active species having high reactivity, a β-modified phosphoric acid compound, a reaction inhibitor, a medicine containing the reaction inhibitor, and a method for inhibiting a reaction, can be provided.

BRIEF DESCRIPTION OF DRAWINGS

FIG. 1 is an explanatory diagram showing the reaction inhibition mechanism by a β-modified phosphoric acid compound precursor.

FIG. 2 is an NMR spectrum showing the results of the experiment of cleavage of the phosphoric acid moiety in Examples.

FIG. 3 is a graph showing the antiproliferative effect of hepatitis B virus in Examples.

FIG. 4 is a graph showing the results of the irreversible inhibition experiment in Examples.

FIG. 5 is a graph showing the results of the anti-HBV activity evaluation in Examples.

DESCRIPTION OF THE INVENTION

1. Partial Structure (1) β-Modified Phosphoric Acid Compound Precursor

Hereinafter, the β-modified phosphoric acid compound precursor according to the present invention will be described. The β-modified phosphoric acid compound precursor according to the present invention is a β-modified phosphoric acid compound precursor to be phosphorylated by phosphorylation, and has a partial structure represented by the following formula 1A in the molecule thereof. [Chemical Formula 12]

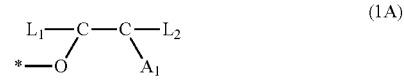

(1A)

(In the formula, $A_1$ represents —S$R_1$, —S—S—$R_1$, —Se$R_1$, or —X (where X means a halogen selected from fluoro, chloro, bromo, and iodo), $R_1$ represents hydrogen, an alkyl group having 1 to 20 carbon atoms, an aryl group having 1 to 20 carbon atoms, or an alkenyl group having 1 to 20 carbon atoms, $L_1$ represents hydrogen, an alkyl group having 1 to 20 carbon atoms, an aryl group having 1 to 20 carbon atoms, or an alkenyl group having 1 to 20 carbon atoms, $L_2$ represents an alkyl group having 1 to 20 carbon atoms, an aryl group having 1 to 20 carbon atoms, or an alkenyl group having 1 to 20 carbon atoms, $L_1$ and $L_2$ may be linked to each other to form a 4 to 6-membered ring structure, the ring structure includes one or more kinds of elements selected from carbon, nitrogen, oxygen, and sulfur, $L_1$ and $L_2$ may each have 1 or 2 or more substituents selected from a hydroxyl group, a carboxyl group, an amino group, an alkyl group, an aryl group, a phospholipid containing one or more saturated and/or unsaturated fatty acids each having 15 to 30 carbon atoms, a monophosphate group, diphosphate group, or triphosphate group, and a base (where the base means adeninyl, guaninyl, cytosinyl, thyminyl, uracilyl, N-methyladeninyl, N-benzoyladeninyl, 2-methylthioadeninyl, 2-aminoadeninyl, 7-methylguaninyl, N-isobutyrylguaninyl, 5-fluorocytosinyl, 5-bromocytosinyl, 5-methylcytosinyl, 4-N-methylcytosinyl, 4-N,N-dimethylcytosinyl, 5-fluorouracilyl, 5-bromouracilyl, 5-chlorouracilyl, or 5,6-dihydrouracilyl), and the symbol * represents a bond to be bonded to a phosphate group by phosphorylation, and means bonding of hydrogen or a substituent other than a phosphate group before the phosphorylation.)

In this regard, it is preferred that $R_1$ is selected from hydrogen, an alkyl group having 1 to 10 carbon atoms, an aryl group having 1 to 10 carbon atoms, and an alkenyl group having 1 to 10 carbon atoms, and it is particularly preferred that $R_1$ is selected from hydrogen, an alkyl group having 1 to 6 carbon atoms, an aryl group having 1 to 6 carbon atoms, and an alkenyl group having 1 to 6 carbon atoms.

Examples of the alkyl group having 1 to 10 carbon atoms include a methyl group, an ethyl group, a propyl group, an isopropyl group, a 2-propenyl group, a butyl group, a pentyl group, a hexyl group, a 2-ethylhexyl group, a heptyl group, an octyl group, a nonyl group, and a decyl group. Examples of the aryl group having 1 to 10 carbon atoms include a phenyl group, an o-tolyl group, a p-tolyl group, a 2,3-dimethylphenyl group, a 2,4-dimethylphenyl group, a 2,5-dimethylphenyl group, a 2,6-dimethylphenyl group, a mesityl group, and an o-cumenyl group. Examples of the alkenyl group having 1 to 6 carbon atoms include a vinyl group, a 1-propenyl group, a 2-propenyl group, and a 1-hexenyl group. The same applies to the following description.

Further, $L_1$ and $L_2$ may be the same as or different from each other, are each preferably selected from hydrogen, an alkyl group having 1 to 10 carbon atoms, an aryl group having 1 to 10 carbon atoms, and an alkenyl group having 1 to 10 carbon atoms, and are each particularly preferably selected from hydrogen, an alkyl group having 1 to 6 carbon atoms, an aryl group having 1 to 6 carbon atoms, and an alkenyl group having 1 to 6 carbon atoms.

In a case where $L_1$ and $L_2$ are linked to each other to form a ring structure, cyclohexane, benzene, pentose, hexose, and the like can be mentioned. $L_1$ and $L_2$ may each have a substituent, and the substituent is selected from a hydroxyl group, a carboxyl group, an amino group, an alkyl group, an aryl group, a phospholipid containing one or more saturated and/or unsaturated fatty acids each having 15 to 30 carbon atoms, and a base. For example, in a case where $L_1$ and $L_2$ are ribose or deoxyribose, a nucleoside derivative is formed when a base is bound at the 1'-position as a substituent.

The base may be a natural nucleobase or a non-natural (synthetic) nucleobase. Examples of the natural nucleobase include adeninyl, guaninyl, cytosinyl, thyminyl, and uracilyl. Examples of the non-natural nucleobase include N-methyladeninyl, N-benzoyladeninyl, 2-methylthioadeninyl, 2-aminoadeninyl, 7-methylguaninyl, N-isobutyrylguaninyl, 5-fluorocytosinyl, 5-bromocytosinyl, 5-methylcytosinyl, 4-N-methylcytosinyl, 4-N,N-dimethylcytosinyl, 5-fluorouracilyl, 5-bromouracilyl, 5-chlorouracilyl, and 5,6-dihydrouracilyl.

The symbol * represents a bond, and means bonding of hydrogen or a substituent other than a phosphate group before the phosphorylation. Before the phosphorylation, in particular, it is preferred that the symbol * means the bonding of hydrogen (that is, *—O is a hydroxyl group).

It can be said that the β-modified phosphoric acid compound precursor represented by the above formula 1A is a compound in which the carbon at the β-position, which is adjacent to the carbon at the α-position bonded to oxygen to be subjected to phosphorylation, is modified with the above $A_1$, in a compound to be phosphorylated. The phosphorylation may be a reaction either in vivo or in vitro, but as the β-modified phosphoric acid compound precursor for medicinal use, an analog of a biological compound to be phosphorylated in vivo is preferable. Examples of the biological compound to be phosphorylated in vivo include a gene-related substance such as a nucleoside, a nucleotide, or a nucleic acid, to be described later, and a metabolism-related substance such as mevalonic acid, or an inositol phosphate, to be described later.

(2) β-Modified Phosphoric Acid Compound

Next, the β-modified phosphoric acid compound will be described. The β-modified phosphoric acid compound according to the present invention is a compound in which the oxygen bonded to the carbon at the α-position is phosphorylated in the β-modified phosphoric acid compound precursor represented by formula 1A. Specifically, the β-modified phosphoric acid compound according to the present invention is a β-modified phosphoric acid compound having a partial structure represented by the following formula 1B.

[Chemical Formula 13]

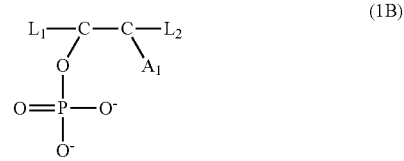

(1B)

(In the formula, $A_1$ represents —$SR_1$, —S—S—$R_1$, —$SeR_1$, or —X (where X means a halogen selected from fluoro, chloro, bromo, and iodo), $R_1$ is selected from hydrogen, an alkyl group having 1 to 20 carbon atoms, an aryl group having 1 to 20 carbon atoms, and an alkenyl group having 1 to 20 carbon atoms, $L_1$ represents hydrogen, an alkyl group having 1 to 20 carbon atoms, an aryl group having 1 to 20 carbon atoms, or an alkenyl group having 1 to 20 carbon atoms, $L_2$ represents an alkyl group having 1 to 20 carbon atoms, an aryl group having 1 to 20 carbon atoms, or an alkenyl group having 1 to 20 carbon atoms, $L_1$ and $L_2$ may be linked to each other to form a 4 to 6-membered ring structure, the ring structure includes one or more kinds of elements selected from carbon, nitrogen, oxygen, and sulfur, and $L_1$ and $L_2$ may each have 1 or 2 or more substituents selected from a hydroxyl group, a carboxyl group, an amino group, an alkyl group, an aryl group, a phospholipid containing one or more saturated and/or unsaturated fatty acids each having 15 to 30 carbon atoms, a monophosphate group, diphosphate group, or triphosphate group, and a base (where the base means adeninyl, guaninyl, cytosinyl, thyminyl, uracilyl, N-methyladeninyl, N-benzoyladeninyl, 2-methylthioadeninyl, 2-aminoadeninyl, 7-methylguaninyl, N-isobutyrylguaninyl, 5-fluorocytosinyl, 5-bromocytosinyl, 5-methylcytosinyl, 4-N-methylcytosinyl, 4-N,N-dimethylcytosinyl, 5-fluorouracilyl, 5-bromouracilyl, 5-chlorouracilyl, or 5,6-dihydrouracilyl).)

(3) Reaction Inhibitor and Method for Inhibiting Reaction

Next, the reaction inhibitor and the method for inhibiting a reaction will be described. The reaction inhibitor according to the present invention is a reaction inhibitor for inhibiting progress of a reaction after phosphorylation in a reaction involving the phosphorylation, and contains a β-modified phosphoric acid compound precursor having a partial structure represented by the above formula 1A in the molecule thereof. Further, the β-modified phosphoric acid compound precursor represented by the above formula 1A is phosphorylated to generate the β-modified phosphoric acid compound represented by the above formula 1B. This β-modified phosphoric acid compound inhibits a reaction after the phosphorylation by the following reaction mechanism.

Hereinafter, the method for inhibiting a reaction (reaction mechanism) according to the present invention will be described. In the method for inhibiting a reaction using the reaction inhibitor described above, first, a β-modified phosphoric acid compound precursor having a partial structure represented by the above formula 1A in the molecule thereof is prepared (step 1).

Next, the β-modified phosphoric acid compound precursor is phosphorylated to generate a β-modified phosphoric acid compound having a partial structure represented by formula 1B in the molecule thereof (step 2). The compound represented by formula 1B generated at this time has an unstable structure, and is partially cleaved to generate an active species represented by the following formula 1C.
[Chemical Formula 14]

(1C)

(In the formula, $A_2$ represents —S—, —S$^+$R$_1$—, —S$^+$—S—R$_1$—, —Se$^+$R$_1$—, or —X$^+$— (where X means a halogen selected from fluoro, chloro, bromo, and iodo), $R_1$ represents hydrogen, an alkyl group having 1 to 20 carbon atoms, an aryl group having 1 to 20 carbon atoms, or an alkenyl group having 1 to 20 carbon atoms, $L_1$ represents hydrogen, an alkyl group having 1 to 20 carbon atoms, an aryl group having 1 to 20 carbon atoms, or an alkenyl group having 1 to 20 carbon atoms, $L_2$ represents an alkyl group having 1 to 20 carbon atoms, an aryl group having 1 to 20 carbon atoms, or an alkenyl group having 1 to 20 carbon atoms, $L_1$ and $L_2$ may be linked to each other to form a 4 to 6-membered ring structure, the ring structure includes one or more kinds of elements selected from carbon, nitrogen, oxygen, and sulfur, and $L_1$ and $L_2$ may each have 1 or 2 or more substituents selected from a hydroxyl group, a carboxyl group, an amino group, an alkyl group, an aryl group, a phospholipid containing one or more saturated and/or unsaturated fatty acids each having 15 to 30 carbon atoms, a monophosphate group, diphosphate group, or triphosphate group, and a base (where the base means adeninyl, guaninyl, cytosinyl, thyminyl, uracilyl, N-methyladeninyl, N-benzoyladeninyl, 2-methylthioadeninyl, 2-aminoadenineaminoadeninyl, 7-methylguaninyl, N-isobutyrylguaninyl, 5-fluorocytosinyl, 5-bromocytosinyl, 5-methylcytosinyl, 4-N-methylcytosinyl, 4-N,N-dimethylcytosinyl, 5-fluorouracilyl, 5-bromouracilyl, 5-chlorouracilyl, or 5,6-dihydrouracilyl).)

This active species is highly reactive, and has a property of nucleophilically attacking another compound to easily form a covalent bond. For example, in a case where $A_2$ is —S—, α and β-carbons and a sulfur atom form a thiirane ring in the molecule. This thiirane ring reacts with a functional group such as an amino group, a thiol group, a hydroxyl group, or an imidazoyl group, and easily forms a covalent bond, and therefore, the thiirane ring is easily covalently bound to a side chain moiety of an amino acid such as lysine, cysteine, tyrosine, histidine, or tryptophan in the molecule of a protein. It is presumed that the active species irreversibly covalently binds to a protein, as a result of which the subsequent reaction is terminated, and thus the reaction inhibitory action is exerted.

Examples of the reaction of inhibition by the β-modified phosphate compound precursor include various reactions involving phosphorylation. In particular, the β-modified phosphate compound precursor can efficiently inhibit the reaction in vivo. The molecule to which an active species binds is not limited to a protein and binds to various molecules, and the reaction is inhibited.

As described above, in the present invention, by using the β-modified phosphoric acid compound precursor, it becomes possible to generate an active species by phosphorylation and irreversibly inhibit a reaction by the covalent bonding. Further, the reaction can be inhibited by specializing for a reaction in which phosphorylation is performed, and therefore, the side effects and the like are hardly generated. In addition, there is an advantage that a compound of a reaction inhibitor targeting a specific reaction can be designed on the basis of the partial structure represented by formula 1A.

(4) Medicine

Since the reaction inhibitor according to the present invention inhibits the reaction after phosphorylation as described above, the reaction inhibitor is useful as an active component in drugs such as medicine, and agricultural chemicals, and is particularly preferably used for medicine. Examples of the form of the medicine include a tablet, a capsule, a pill, powder, granules, fine granules, a jelly, and a liquid.

The above-described drug may contain additives such as a solvent, an excipient, a binding agent, a disintegrant, a lubricating agent, a stabilizer, and a suspending agent within the range not impairing the reaction inhibitory effect of the present invention, in addition to the reaction inhibitor according to the present invention. Examples of the solvent for pharmaceutical preparation include water, ethanol, and glycerin. Examples of the excipient include lactose, white soft sugar, glucose, mannitol, sorbitol, corn starch, potato starch, α-starch, dextrin, carboxymethyl starch, crystal cellulose, hydroxypropyl methyl cellulose, carboxymethyl cellulose, carboxymethyl cellulose calcium, gum arabic, dextran, pullulan, a silicate such as light anhydrous silicic acid, synthetic aluminum silicate, or magnesium aluminometasilicate, calcium phosphate, calcium carbonate, and calcium sulfate. Examples of the binding agent include gelatin, polyvinyl pyrrolidone, and macrogol. Examples of the disintegrant include croscarmellose sodium, sodium carboxymethyl starch, and cross-linked polyvinyl pyrrolidone. Examples of the lubricating agent include talc, stearic acid, calcium stearate, magnesium stearate, colloidal silica, Veegum, beeswax, spermaceti, boric acid, glycol, fumaric acid, adipic acid, sodium benzoate, sodium sulfate, leucine, sodium lauryl sulfate, magnesium lauryl sulfate, silicic anhydride, and silicic acid hydrate. Examples of the stabilizer include methylparaben, propylparaben, chlorobutanol, benzyl alcohol, phenylethyl alcohol, benzalkonium chloride, phenol, cresol, thimerosal, acetic anhydride, and sorbic acid. Examples of the suspending agent include polysorbate 80, and sodium carboxymethyl cellulose.

(5) Method for Producing β-Modified Phosphoric Acid Compound Precursor

Next, a method for producing a β-modified phosphoric acid compound precursor will be described. The β-modified phosphoric acid compound precursor represented by formula 1A can be synthesized by a scheme of the following formula. Specifically, a compound in which a hydroxyl group or the like is bonded to the carbon at the β-position is used as a starting material, and a protecting group is bonded to a hydroxyl group other than the hydroxyl group bonded to the carbon at the β-position for the protection. Next, the hydroxyl group bonded to the β-carbon is replaced with $A_1$, and finally the protecting group is eliminated, as a result of which the compound represented by formula 1A can be synthesized. The types of the starting material and the protecting group, the reaction conditions (concentration, temperature, etc.), and the like vary depending on the β-modified phosphoric acid compound precursor to be synthesized.

[Chemical Formula 15]

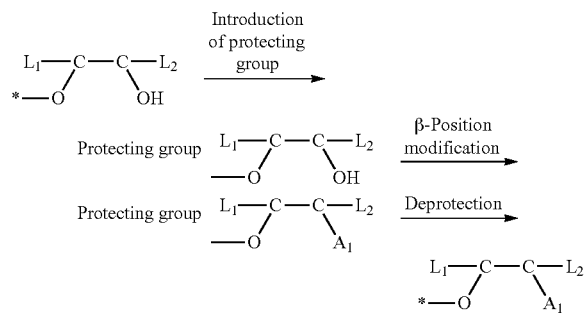

Examples of the β-modified phosphoric acid compound precursor include various specific compounds. Hereinafter, a nucleoside derivative, a mevalonic acid derivative, and a phosphatidylinositol derivative each will be described in detail.

2. Nucleoside Derivative (1) β-Modified Phosphoric Acid Compound Precursor

As the β-modified phosphoric acid compound precursor, a nucleoside derivative represented by the following formula 2A can be mentioned.

[Chemical Formula 16]

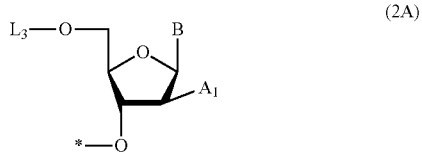

(2A)

(In the formula, $A_1$ represents —$SR_1$, —S—S—$R_1$, —$SeR_1$, or —X (where X means a halogen selected from fluoro, chloro, bromo, and iodo), $R_1$ is hydrogen, an alkyl group having 1 to 20 carbon atoms, an aryl group having 1 to 20 carbon atoms, or an alkenyl group having 1 to 20 carbon atoms, $L_3$ represents hydrogen, or a monophosphate group, diphosphate group, or triphosphate group represented by the following formula 2D,

[Chemical Formula 17]

(2D)

(where n is an integer of 1 to 3, $Z_1$ represents a hydroxyl group, or a methyl ester, ethyl ester, isopropyl ester, n-butyl ester, benzyl ester, or phenyl ester of glycine, alanine, valine, leucine, phenylalanine, tryptophan, methionine, or proline, $Z_2$ represents hydrogen, an alkyl group having 1 to 4 carbon atoms, a halogen, or a phenyl group, and $Z_1$s may be the same as or different from each other in a case where n is 2 or more.), B represents a base selected from adeninyl, guaninyl, cytosinyl, thyminyl, uracilyl, N-methyladeninyl, N-benzoyladeninyl, 2-methylthioadeninyl, 2-aminoadeninyl, 7-methylguaninyl, N-isobutyrylguaninyl, 5-fluorocytosinyl, 5-bromocytosinyl, 5-methylcytosinyl, 4-N-methylcytosinyl, 4-N,N-dimethylcytosinyl, 5-fluorouracilyl, 5-bromouracilyl, 5-chlorouracilyl, or 5,6-dihydrouracilyl, and the symbol * represents a bond to be bonded to a phosphate group by phosphorylation, and means bonding of hydrogen or a substituent other than a phosphate group before the phosphorylation.)

In this regard, specific examples of the nucleoside derivative include the compounds shown below, but the nucleoside derivative is not limited to the compounds.

Examples of an adenosine derivative in which the base is adenine include the compounds represented by the following formulas (2A-1A) to (2A-12A).

[Chemical Formula 18]

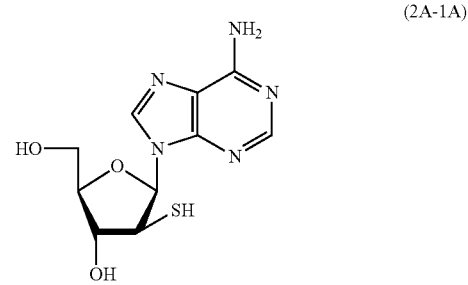

(2A-1A)

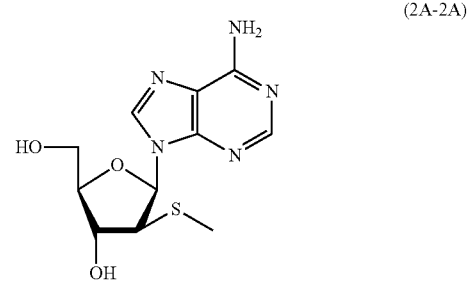

(2A-2A)

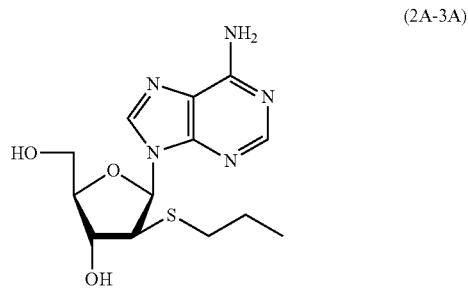

(2A-3A)

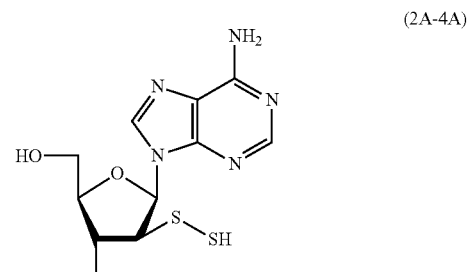

(2A-4A)

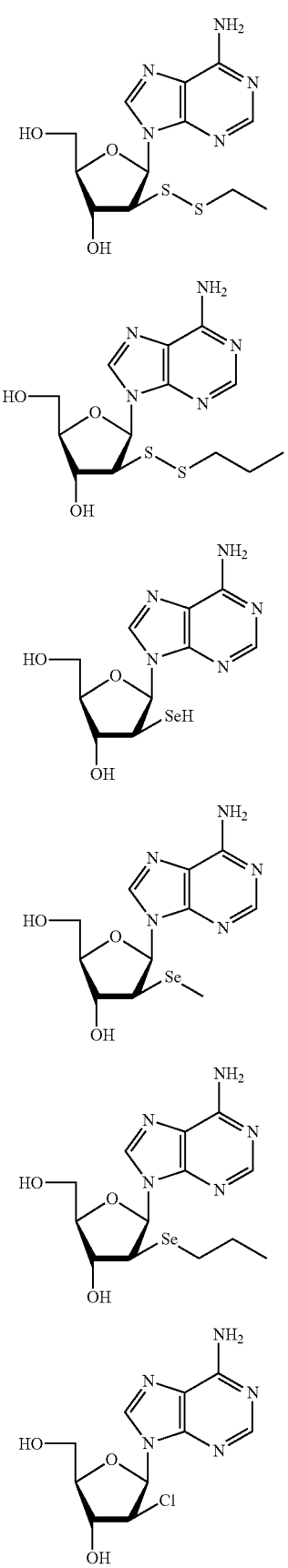
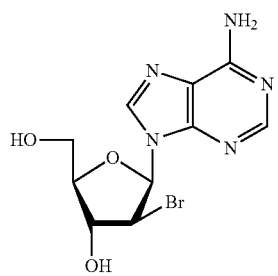
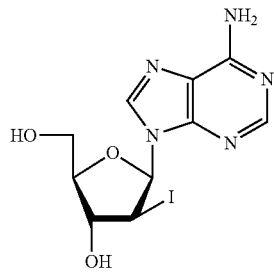
Examples of a guanosine derivative in which the base is guanine include the compounds represented by the following formulas (2A-1G) to (2A-12G).
[Chemical Formula 19]
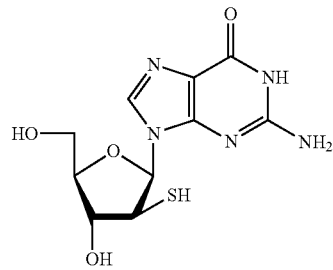
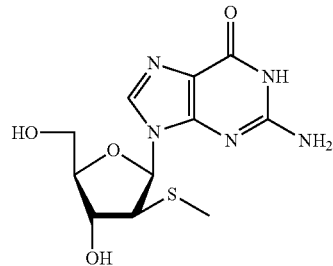
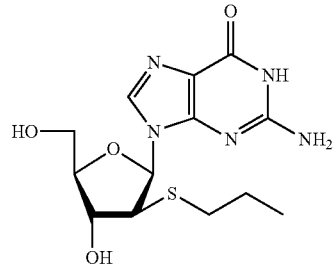

(2A-4G)
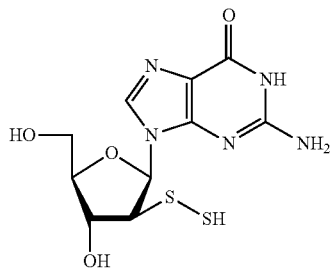
(2A-5G)
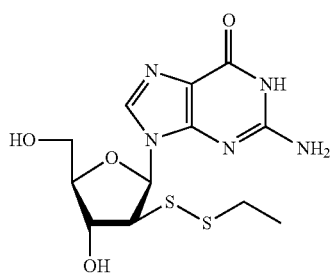
(2A-6G)
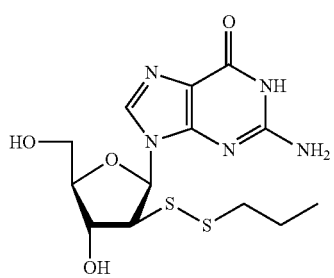
(2A-7G)
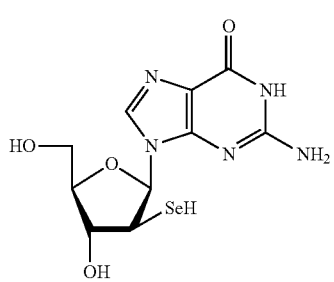
(2A-8G)
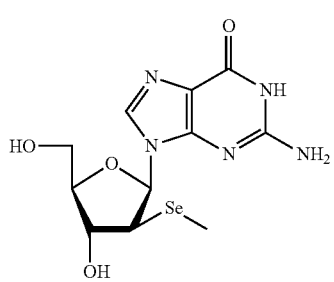
(2A-9G)
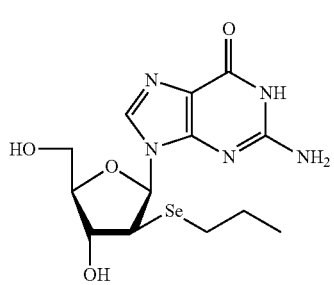
(2A-10G)
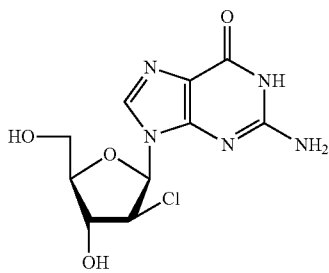
(2A-11G)
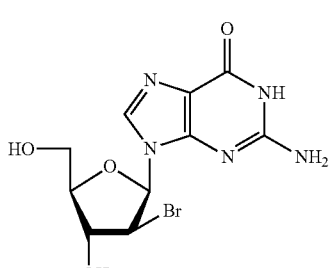
(2A-12G)
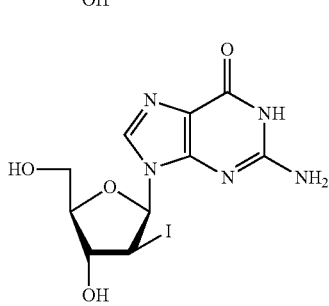
Examples of a cytidine derivative in which the base is cytosine include the compounds represented by the following formulas (2A-1C) to (2A-12C).
[Chemical Formula 20]
(2A-1C)
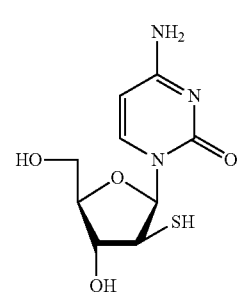
(2A-2C)
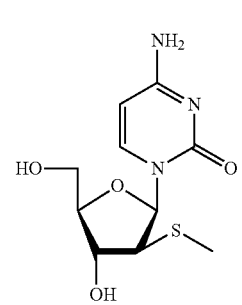

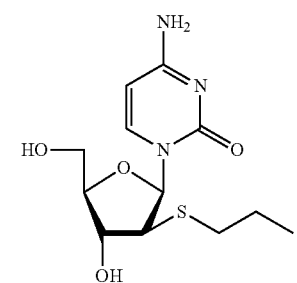
(2A-3C)
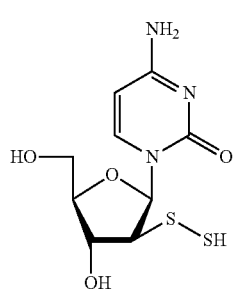
(2A-4C)
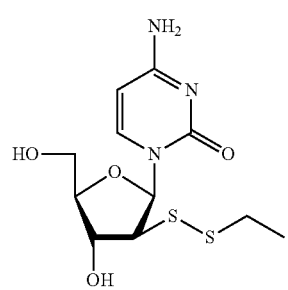
(2A-5C)
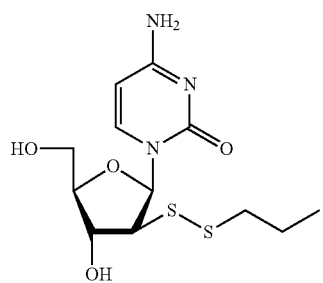
(2A-6C)
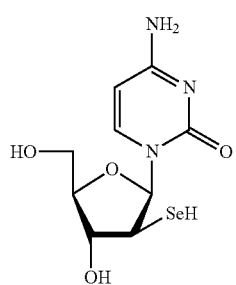
(2A-7C)
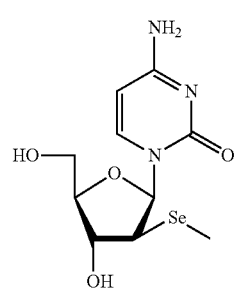
(2A-8C)
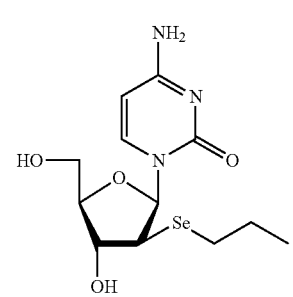
(2A-9C)
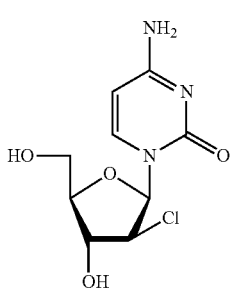
(2A-10C)
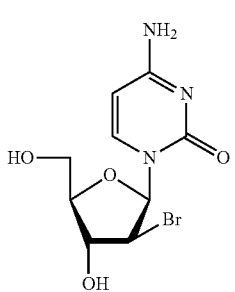
(2A-11C)
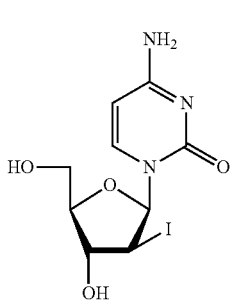
(2A-12C)

Examples of a thymidine derivative in which the base is thymine include the compounds represented by the following formulas formulas (2A-1T) to (2A-12T).
[Chemical Formula 21]
(2A-1T)
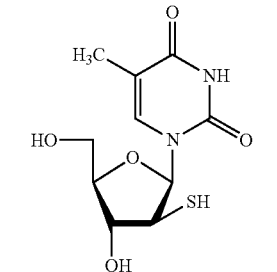
(2A-2T)
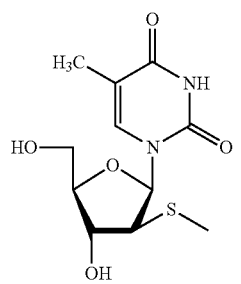
(2A-3T)
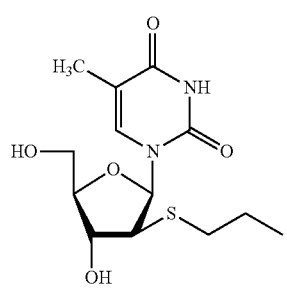
(2A-4T)
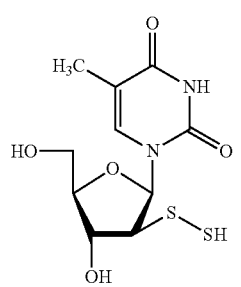
(2A-5T)
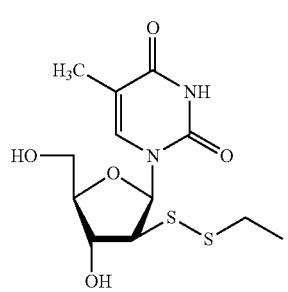
-continued
(2A-6T)
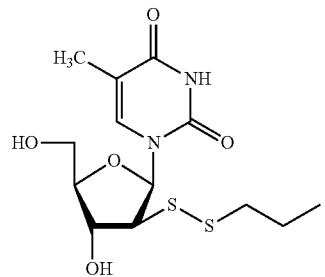
(2A-7T)
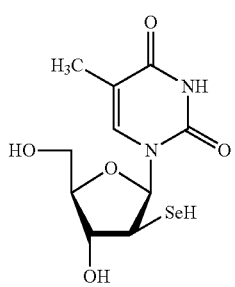
(2A-8T)
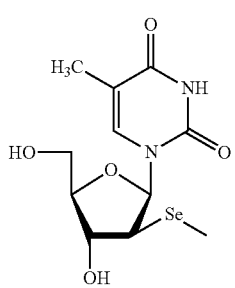
(2A-9T)
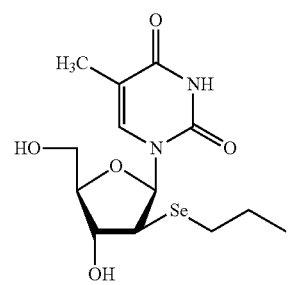
(2A-10T)
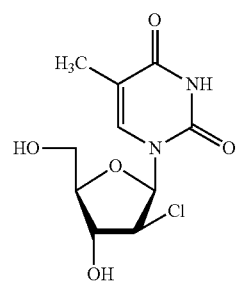

(2A-11T)
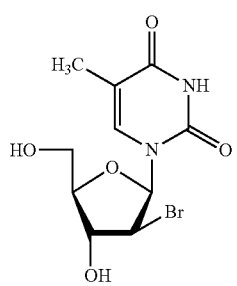
(2A-12T)
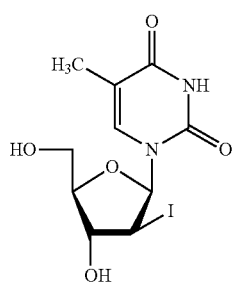
Examples of a uridine derivative in which the base is uracil include the compounds represented by the following formulas (2A-1) to (2A-2U).
[Chemical Formula 22]
(2A-1U)
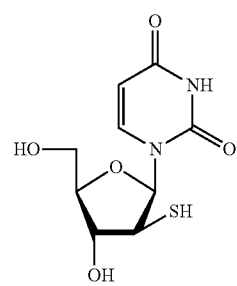
(2A-2U)
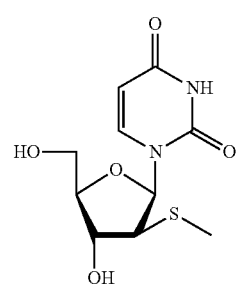
(2A-3U)
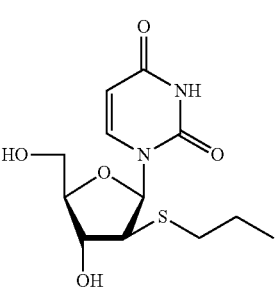
(2A-4U)
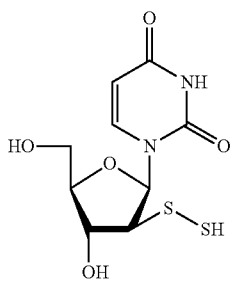
(2A-5U)
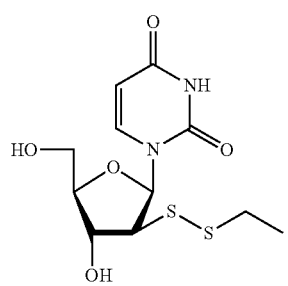
(2A-6U)
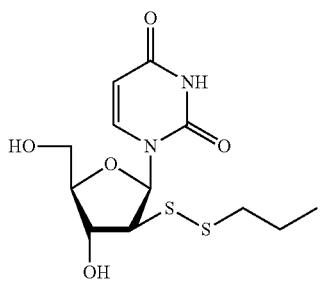
(2A-7U)
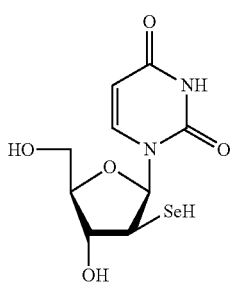
(2A-8U)
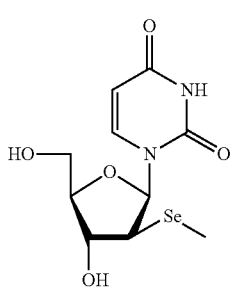

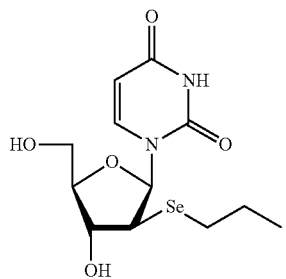
(2A-9U)

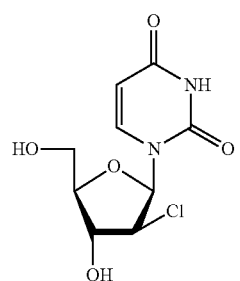
(2A-10U)

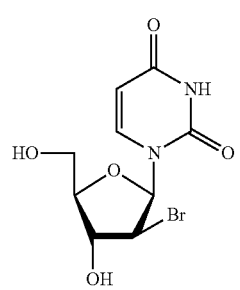
(2A-11U)

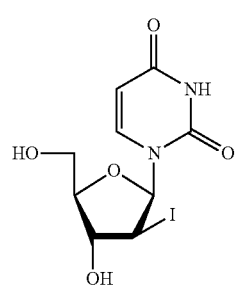
(2A-12U)

In the nucleoside derivative in the present invention, a nucleotide or a derivative thereof (in a case where $L_3$ is a monophosphate group, a diphosphate group, or a triphosphate group, or a derivative thereof) is also included. Examples of the nucleotide or a derivative thereof include the compounds in which $L_3$ is the above formula 2D. In this regard, in a case where the nucleoside derivative is a nucleotide, a case corresponds where $Z_1$ is a hydroxyl group and $Z_2$ is hydrogen in formula 2D. Further, a case where the nucleoside derivative is a nucleotide derivative, a case corresponds where $Z_1$ is a methyl ester, ethyl ester, isopropyl ester, n-butyl ester, benzyl ester, or phenyl ester of glycine, alanine, valine, leucine, phenylalanine, tryptophan, methionine, or proline, and $Z_2$ is an alkyl group having 1 to 4 carbon atoms, a halogen, or a phenyl group, in formula 2D. In this case, $Z_1$ is preferably an alanine isopropyl ester, an alanine cyclohexyl ester, an alanine neopentyl ester, a valine isopropyl ester, or a leucine isopropyl ester. These esters bind phosphorus via the nitrogen derived from an amino acid such as glycine. Further, $Z_2$ is preferably a phenyl group.

In addition, as the β-modified phosphoric acid compound precursor, a nucleic acid having a nucleoside derivative represented by the above formula 2A at the 3'-end can be mentioned. In this regard, the nucleic acid may be either deoxyribonucleic acid (DNA) or ribonucleic acid (RNA), and in a case of DNA, the DNA may be either double-stranded DNA or single-stranded DNA. The number of structural units of the nucleic acid is not particularly limited, and is usually within the range of 1 to 100 bases (base pairs in a case of double-stranded DNA), preferably within the range of 1 to 50 bases (base pairs), and more preferably within the range of 1 to 10 bases (base pairs).

(2) β-Modified Phosphoric Acid Compound

As the β-modified phosphoric acid compound after the phosphorylation of the nucleoside derivative represented by the above formula 2A, a β-modified phosphoric acid compound having a partial structure represented by the following formula 2B can be mentioned.

[Chemical Formula 23]

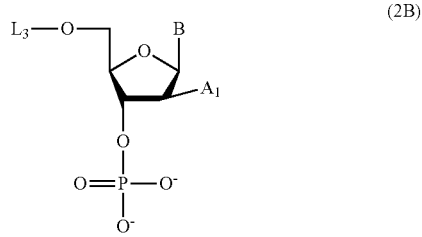
(2B)

(In the formula, $A_1$ represents $-SR_1$, $-S-S-R_1$, $-SeR_1$, or $-X$ (where X means a halogen selected from fluoro, chloro, bromo, and iodo), $R_1$ represents hydrogen, an alkyl group having 1 to 20 carbon atoms, an aryl group having 1 to 20 carbon atoms, or an alkenyl group having 1 to 20 carbon atoms, $L_3$ represents hydrogen, or a monophosphate group, diphosphate group, or triphosphate group represented by the above formula 2D, and B represents a base selected from adeninyl, guaninyl, cytosinyl, thyminyl, uracilyl, N-methyladeninyl, N-benzoyladeninyl, 2-methylthioadeninyl, 2-aminoadeninyl, 7-methylguaninyl, N-isobutyrylguaninyl, 5-fluorocytosinyl, 5-bromocytosinyl, 5-methylcytosinyl, 4-N-methylcytosinyl, 4-N,N-dimethylcytosinyl, 5-fluorouracilyl, 5-bromouracilyl, 5-chlorouracilyl, or 5,6-dihydrouracilyl.)

Further, as the β-modified phosphoric acid compound, a nucleic acid having a nucleoside derivative represented by the above formula 2B at the 3'-end can be mentioned. In this regard, the nucleic acid may be either deoxyribonucleic acid (DNA) or ribonucleic acid (RNA), and in a case of DNA, the DNA may be either double-stranded DNA or single-stranded DNA. The number of structural units of the nucleic acid is not particularly limited, and is usually within the range of 1 to 100 bases (base pairs in a case of double-stranded DNA), preferably within the range of 1 to 50 bases (base pairs), and more preferably within the range of 1 to 10 bases (base pairs).

(3) Reaction Inhibitor and Method for Inhibiting Reaction

In a case where the β-modified phosphoric acid compound precursor is a nucleoside derivative represented by formula 2A and the β-modified phosphoric acid compound is a nucleoside derivative represented by the above formula 2B, a compound represented by the following formula 2C is generated as an active species that is an intermediate.
[Chemical Formula 24]

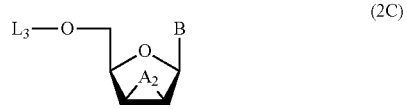

(In the formula, $A_2$ represents —S—, —S$^+$($R_1$)—, —S$^+$(S—$R_1$)—, —Se$^+$($R_1$)—, or —X$^+$— (where X means a halogen selected from fluoro, chloro, bromo, and iodo), $R_1$ is hydrogen, an alkyl group having 1 to 20 carbon atoms, an aryl group having 1 to 20 carbon atoms, or an alkenyl group having 1 to 20 carbon atoms, $L_3$ represents hydrogen, a monophosphate group, a diphosphate group, or a triphosphate group, and B represents a base selected from adeninyl, guaninyl, cytosinyl, thyminyl, uracilyl, N-methyladeninyl, N-benzoyladeninyl, 2-methylthioadeninyl, 2-aminoadeninyl, 7-methylguaninyl, N-isobutyrylguaninyl, 5-fluorocytosinyl, 5-bromocytosinyl, 5-methylcytosinyl, 4-N-methylcytosinyl, 4-N,N-dimethylcytosinyl, 5-fluorouracilyl, 5-bromouracilyl, 5-chlorouracilyl, or 5,6-dihydrouracilyl.)

In a case where the β-modified phosphoric acid compound is a nucleoside derivative represented by formula 2A, particularly a polymerase reaction is efficiently inhibited. The polymerase reaction includes both a DNA polymerase and a RNA polymerase, and the nucleoside derivative represented by formula 2A can suitably inhibit particularly the DNA polymerase. Hereinafter, the DNA polymerase inhibitory action will be described while making reference to drawings.

FIG. 1 is a schematic diagram showing a DNA polymerase inhibitory action in a case where $A_1$ is —S$R_1$ (thioalkyl group), as an example of the nucleoside derivative represented by formula 2A. When the nucleoside derivative is administered in vivo (in a cell), a kinase phosphorylates a 5'-hydroxyl group of the nucleoside derivative to form a nucleoside triphosphate derivative. This serves as a substrate for a DNA polymerase reaction, and binds onto the 3'-end side of the single-stranded DNA that is extended by a DNA polymerase. Next, a 5'-phosphate group of the following nucleoside binds to the 3'-hydroxyl group of the nucleoside derivative (the left side of lower part of FIG. 1). In the reaction intermediate in this state, the 3'-phosphate group is dissociated by a nucleophilic attack of the 2'-thioalkyl group, and a thiirane ring is formed with three elements of the carbon at the 2'-position, the carbon at the 3'-position, and the sulfur of the thioalkyl group (the center of lower part of FIG. 1). This thiirane ring is highly reactive, and it is presumed that the thiirane ring forms a covalent bond by reacting with a side chain of a specific amino acid constituting the DNA polymerase (the right side of lower part of FIG. 1). This reaction is irreversible, and the polymerase reaction does not proceed thereafter. As described above, by using the nucleoside derivative, a reaction can be efficiently inhibited by a novel mechanism of covalently binding to a polymerase and inhibiting the reaction, unlike in a case of the conventional extension inhibition reaction using acyclovir or the like.

In order to inhibit the polymerase reaction, first, the nucleoside derivative represented by formula 2A is added into a biological sample (cell, virus, or the like) to be targeted. The nucleoside derivative is dissolved in an appropriate solvent such as a buffer solution, and then the obtained mixture is added to such a biological sample. The concentration of the nucleoside derivative at the time of addition can be appropriately set depending on the characteristics and the like of the reaction to be targeted. For example, in a case of the hepatitis B virus to be described later, the concentration of the nucleoside derivative is usually within the range of 1 μM to 1 mM, preferably within the range of 10 μM to 500 μM, and particularly preferably within the range of 50 to 200 μM. The reaction time can be appropriately set, and in a case of, for example, hepatitis B virus, the reaction time is usually within the range of 1 to 30 days, and more preferably within the range of 5 to 10 days.

The β-modified phosphoric acid compound precursor inhibits a reaction after phosphorylation in a reaction involving the phosphorylation. The reaction inhibitory activity of the β-modified phosphoric acid compound precursor can be evaluated by quantifying a compound (DNA or RNA in a case of a polymerase reaction) generated by phosphorylation, or further a biological sample itself such as a cell or a virus.

(4) Medicine

The nucleoside derivative is a polymerase inhibitor, and inhibits replication of DNA or transcription of RNA, and therefore, the proliferation or the like of cells and viruses are suppressed. For this reason, the nucleoside derivative represented by formula 2A is a proliferation inhibitor, and is useful as a therapeutic agent for a viral disease, a cancer, or the like.

(5) Method for Producing Nucleoside Derivative Precursor

Hereinafter, a method for producing a nucleoside derivative will be described. Since specific reaction conditions and the like will be described in detail in Examples to be described later, an outline of a synthetic method (production method) for some nucleoside derivatives will be described herein.

(a) Synthesis of Compound of Formula (2A-1A) (·X· Compound in which $A_1$ is —SH)

The synthesis will be described in accordance with the following synthetic scheme. In the synthetic scheme to be described below, the numbers represent the numbers of compounds. First, by using a nucleoside (adenosine in the following scheme) as a starting material, 1,3-dichloro-1,1,3,3-tetraisopropyldisiloxane (TPDSCl$_2$) is reacted in a solvent such as pyridine. As a result, a cyclic structure of siloxane bond is formed between the 3'-hydroxyl group and 5'-hydroxyl group of ribose, and the hydroxyl groups at the 3'-position and the 5'-position are protected (compound 1). Next, N-phenyltrifluoromethanesulfonimide is added, and a nucleophile such as N,N-dimethyl-4-aminopyridine (DMAP) is reacted in a solvent such as dichloromethane (DCM) to change the 2'-position of ribose to have a trifluorosulfonic acid group (compound 2). Next, a compound having a thiol group, such as potassium thioacetate is reacted in the presence of N,N-dimethylformamide (DMF) or the like to form a thioester at the 2'-position of ribose (compound 3). Further, the thioester group is converted to a thiol group by the reaction in an ammonia/methanol solution (compound 4). Subsequently, by the addition of a triethylamine trihydrofluoride (3HF-Et$_3$N) and tetrahydrofuran (THF), the protecting groups at the 3'-position and 5'-position of ribose are eliminated, and the positions are changed to have hydroxyl groups.

[Chemical Formula 25]

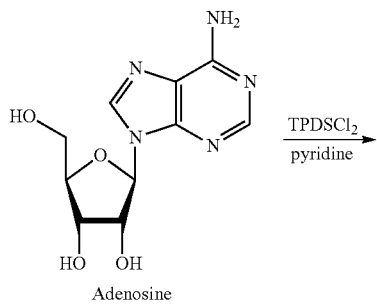
Adenosine

TPDSCl₂ / pyridine →

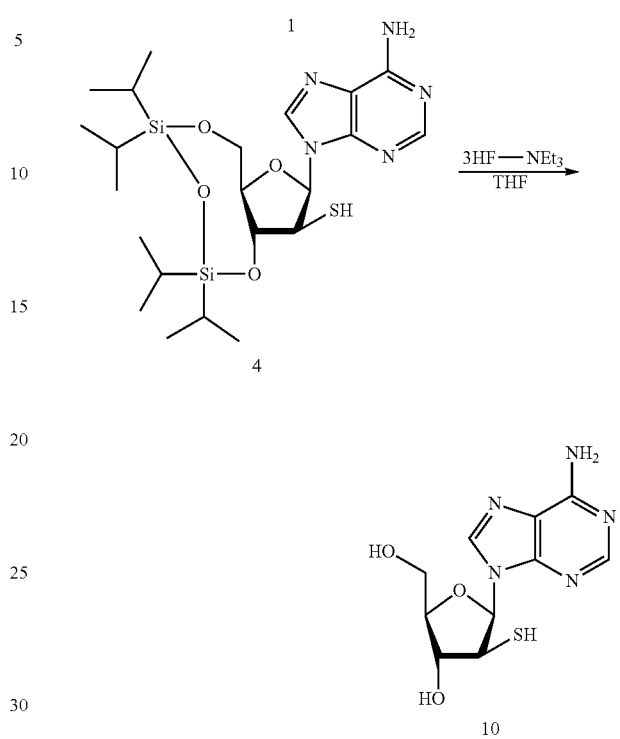

3HF—NEt₃ / THF →

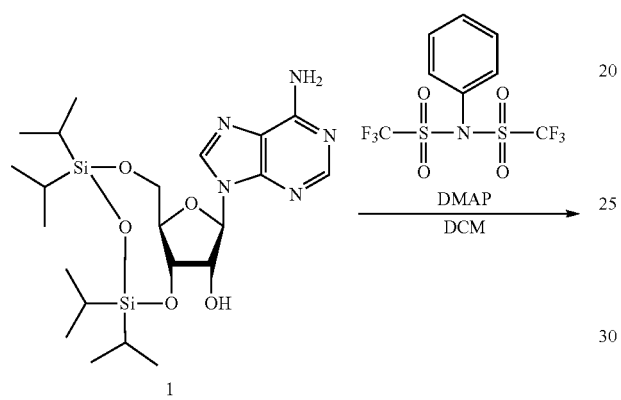
1

F₃C—S(=O)₂—N(Ph)—S(=O)₂—CF₃
DMAP / DCM →

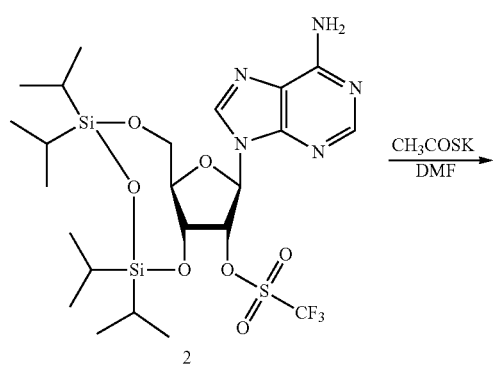
2

CH₃COSK / DMF →

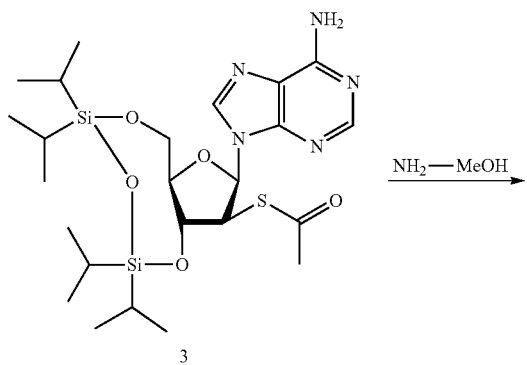
3

NH₂—MeOH →

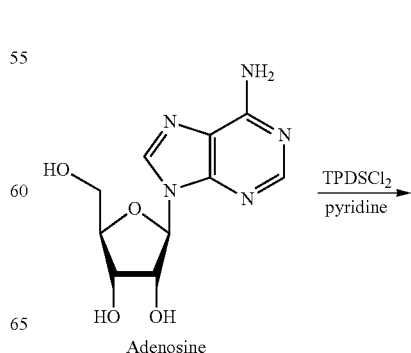
Adenosine

TPDSCl₂ / pyridine →

(b) Synthesis of Compound of Formula (2A-6A) (X: Compound in which A₁ is —S—S—C₃H₅)

The synthetic scheme up to compound 4 is the same as the synthetic scheme in a case of the synthesis of the compound represented by the above formula (2A-1A). Subsequently, reaction with a thioalkyl compound such as 1-propanethiol is conducted in a solvent such as a mixed solvent of tetrahydrofuran (THF) and diisopropyl azodicarboxylate (DIAD) to change the 2'-position of ribose to have a disulfide alkyl group (compound 5). Next, reaction with benzoyl chloride (BzCl) is conducted in a solvent to protect an amino group of a base with a benzoyl group. Subsequently, by the addition of a triethylamine trihydrofluoride (3HF-Et₃N) and THF, the protecting groups at the 3'-position and 5'-position of ribose are eliminated, and the positions are changed to have hydroxyl groups (compound 11).

[Chemical Formula 26]

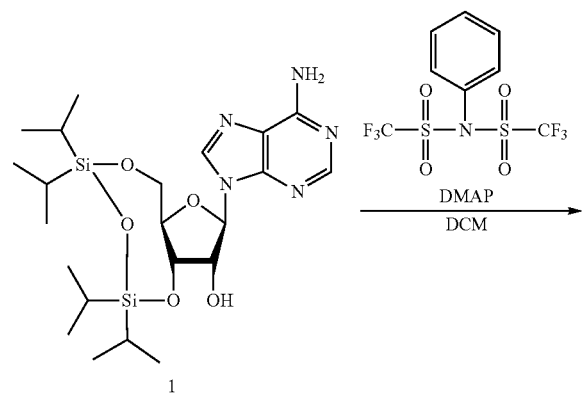

1

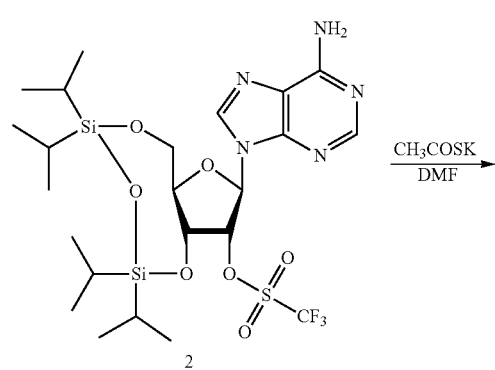

2

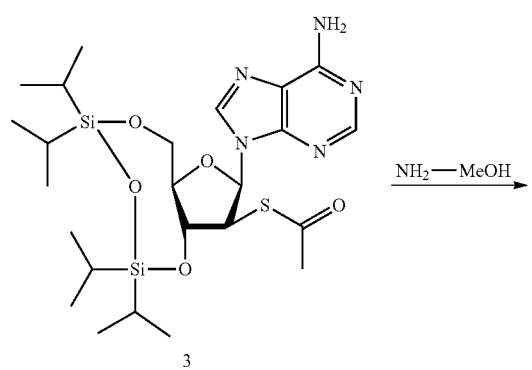

3

4

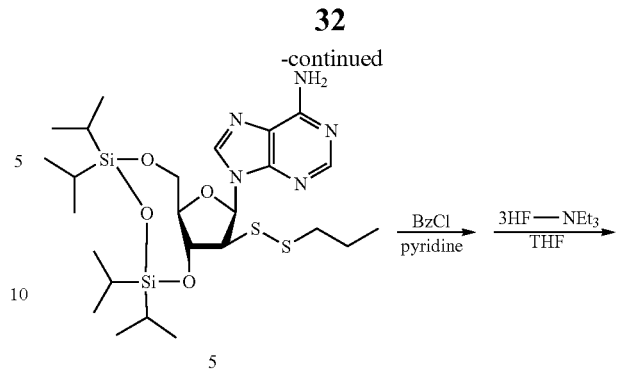

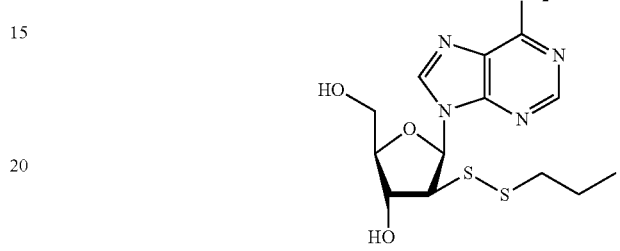

5

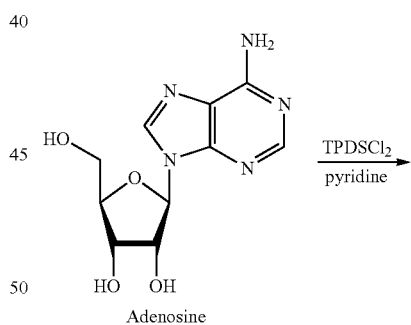

11

(c) Synthesis of Compound of Formula (2A-8A) (✗ Compound in which $A_1$ is —Se—$CH_3$)

The synthetic scheme up to compound 2 is the same as the synthetic scheme in a case of the synthesis of the compound represented by the above formula (2A-1A). Next, reaction is conducted in solvents such as dimethyldiselenide, sodium borohydride, and further THF (compound 12). Further, by the addition of tetra-n-butyl ammonium fluoride (TBAF), THF, and the like, the protecting groups at the 3'-position and 5'-position of ribose are eliminated, and the positions are changed to have hydroxyl groups (compound 13).

[Chemical Formula 27]

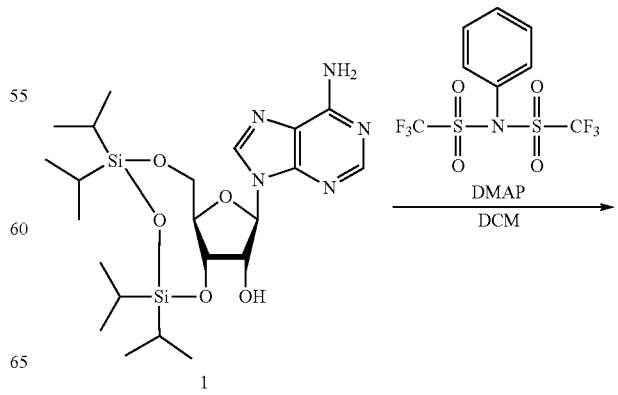

1

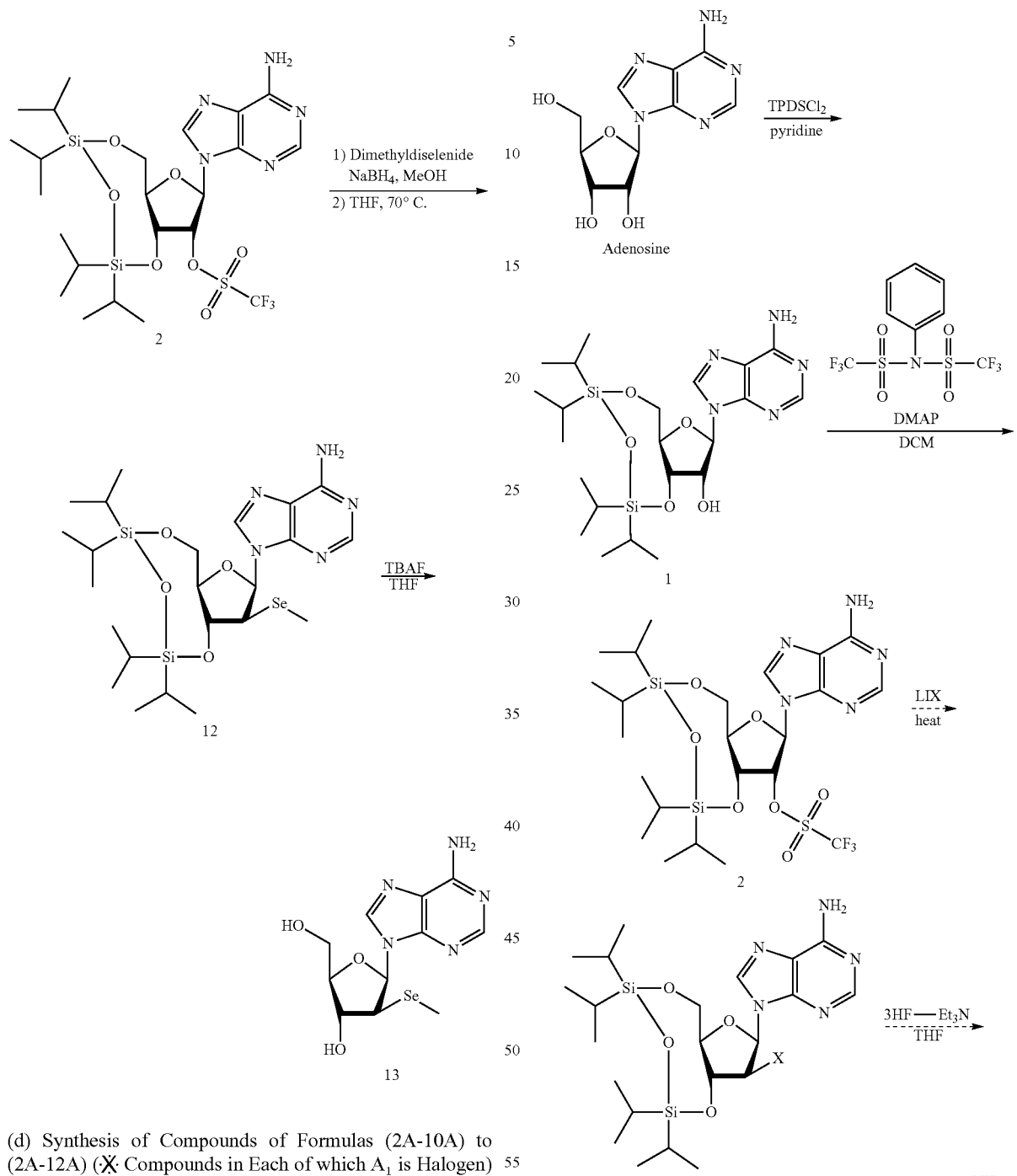

(d) Synthesis of Compounds of Formulas (2A-10A) to (2A-12A) (X: Compounds in Each of which $A_1$ is Halogen)

Next, the synthetic scheme of a halogen compound will be described. The synthetic scheme up to compound 2 is the same as the synthetic scheme in a case of the synthesis of the compound represented by the above formula (2A-1A). Next, by the addition and heating of a lithium halide, the halogen is introduced. Examples of the lithium halide include lithium fluoride, lithium chloride, lithium bromide, and lithium iodide. Subsequently, by the addition of a triethylamine trihydrofluoride (3HF-Et$_3$N) and THF, the protecting groups at the 3'-position and 5'-position of ribose are eliminated, and the positions are changed to have hydroxyl groups.

3. Mevalonic Acid Derivative (1) β-Modified Phosphoric Acid Compound Precursor

As the β-modified phosphoric acid compound precursor, a mevalonic acid derivative represented by the following formula 3A can be mentioned.

[Chemical Formula 29]

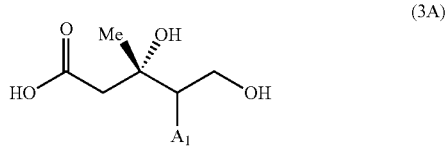

(3A)

(In the formula, $A_1$ represents —$SR_1$, —S—S—$R_1$, —$SeR_1$, or —X (where X means a halogen selected from fluoro, chloro, bromo, and iodo), and $R_1$ represents hydrogen, an alkyl group having 1 to 20 carbon atoms, an aryl group having 1 to 20 carbon atoms, or an alkenyl group having 1 to 20 carbon atoms.)

In particular, a compound in which $A_1$ is —SH, —$SCH_3$, —S—$C_2H_5$, —S—$C_3H_7$, —S—SH, —S—S—$CH_3$, —S—S—$C_2H_5$, —S—S—$C_3H_7$, or the like is preferred.

(2) β-Modified Phosphoric Acid Compound

Further, as the β-modified phosphoric acid compound after the phosphorylation of the mevalonic acid derivative represented by the above formula 3A, a β-modified phosphoric acid compound having a partial structure represented by the following formula 3B can be mentioned.

[Chemical Formula 30]

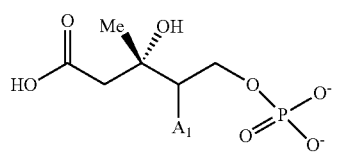

(3B)

(In the formula, $A_1$ represents —$SR_1$, —S—S—$R_1$, —$SeR_1$, or —X (where X means a halogen selected from fluoro, chloro, bromo, and iodo), and $R_1$ represents hydrogen, an alkyl group having 1 to 20 carbon atoms, an aryl group having 1 to 20 carbon atoms, or an alkenyl group having 1 to 20 carbon atoms.)

(3) Reaction Inhibitor and Method for Inhibiting Reaction

In particular, in a case where the β-modified phosphoric acid compound precursor is a mevalonic acid derivative represented by formula 3A and the β-modified phosphoric acid compound is a mevalonic acid derivative represented by the above formula 3B, a compound represented by the following formula 3C is generated as an active species that is an intermediate.

[Chemical Formula 31]

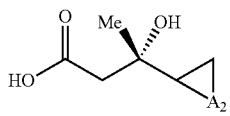

(3C)

(In the formula, $A_2$ represents —S—, —$S^+(R_1)$—, —$S^+(S$—$R_1)$—, —$Se^+(R_1)$—, or —$X^+$— (where X means a halogen selected from fluoro, chloro, bromo, and iodo), and $R_1$ represents hydrogen, an alkyl group having 1 to 20 carbon atoms, an aryl group having 1 to 20 carbon atoms, or an alkenyl group having 1 to 20 carbon atoms.)

Hereinafter, the active species generation reaction of a mevalonic acid derivative represented by formula 3A will be described by way of a specific example (compound in which $A_1$ is —SH). In the mevalonic acid derivative represented by the following formula, sulfur of $A_1$ forms a thiirane ring with a carbon-carbon bond of the skeleton by phosphorylation. This ring structure is extremely unstable, and has a property of easily forming a covalent bond with another compound.

[Chemical Formula 32]

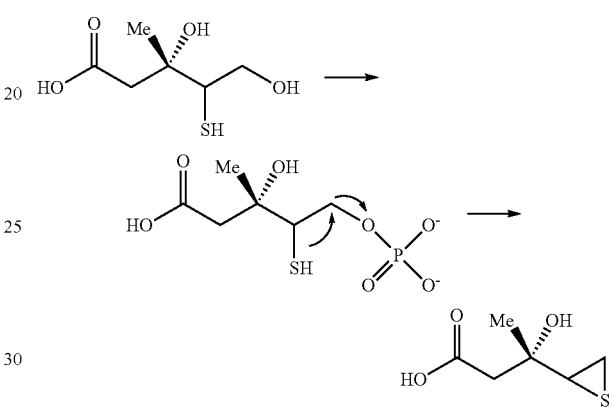

In a case where the β-modified phosphoric acid compound is a mevalonic acid derivative represented by formula 3A, particularly a mevalonate kinase, and a 5-phosphomevalonate kinase are efficiently inhibited. Mevalonic acid is a substance involved in a mevalonate pathway that synthesizes a terpene, and 5-phosphomevalonic acid is formed from mevalonic acid and ATP by the mevalonate kinase, and further 5-diphosphomevalonic acid is formed from the 5-phosphomevalonic acid and ATP by the 5-phosphomevalonate kinase. The mevalonic acid derivative represented by formula 3A serves as an efficient reaction inhibitor of the mevalonate pathway as an analog of the mevalonic acid. That is, it is presumed that the mevalonic acid derivative represented by formula 3A is phosphorylated, an active species represented by formula 3C is generated through the compound represented by formula 3B, and the active species covalently binds to the mevalonate kinase, the 5-phosphomevalonate kinase, or the like, as a result of which the reaction after the phosphorylation is inhibited.

(4) Medicine

Since the mevalonic acid derivative represented by formula 3A inhibits the mevalonate pathway, the generation of cholesterol is suppressed. For this reason, the mevalonic acid derivative represented by formula 3A is a cholesterol generation inhibitor, and is useful as a therapeutic agent for hyperlipidemia, hypercholesterolemia, or the like.

4. Phosphatidylinositol Derivative (1) β-Modified Phosphoric Acid Compound Precursor As the β-modified phosphoric acid compound precursor, a phosphatidylinositol derivative represented by the following formula 4A can be mentioned.

[Chemical Formula 33]

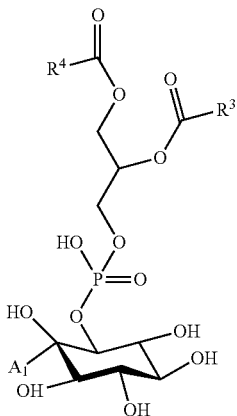

(4A)

(In the formula, $A_1$ represents —$SR_1$, —S—S—$R_1$, —$SeR_1$, or —X (where X means a halogen selected from fluoro, chloro, bromo, and iodo), $R_1$ represents hydrogen, an alkyl group having 1 to 20 carbon atoms, an aryl group having 1 to 20 carbon atoms, or an alkenyl group having 1 to 20 carbon atoms, $R_3$ is an unsaturated fatty acid selected from arachidonic acid, linoleic acid, and linolenic acid, and $R_4$ is a saturated fatty acid selected from stearic acid, and palmitic acid.)

In particular, a compound in which $A_1$ is —SH, —$SCH_3$, —S—$C_2H_5$, —S—$C_3H_7$, —S—SH, —S—S—$CH_3$, —S—S—$C_2H_5$, —S—S—$C_3H_7$, or the like is preferred.

(3) Reaction Inhibitor and Method for Inhibiting Reaction

In particular, in a case where the β-modified phosphoric acid compound precursor is a phosphatidylinositol derivative represented by formula 4A and the β-modified phosphoric acid compound is a phosphatidylinositol derivative represented by the above formula 4B, a compound represented by the following formula 4C is generated as an active species that is an intermediate.

[Chemical Formula 34]

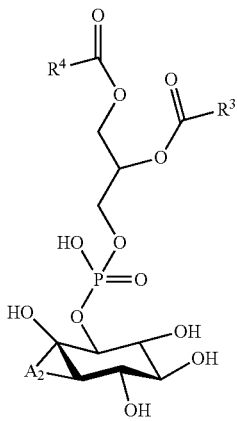

(4C)

(In the formula, $A_2$ represents —S—, —$S^+(R_1)$—, —$S^+(S—R_1)$—, —$Se^+(R_1)$—, or —$X^+$— (where X means a halogen selected from fluoro, chloro, bromo, and iodo), $R_1$ represents hydrogen, an alkyl group having 1 to 20 carbon atoms, an aryl group having 1 to 20 carbon atoms, or an alkenyl group having 1 to 20 carbon atoms, $R_3$ is an unsaturated fatty acid selected from arachidonic acid, linoleic acid, and linolenic acid, and $R_4$ is a saturated fatty acid selected from stearic acid, and palmitic acid.)

Hereinafter, the active species generation reaction of phosphatidylinositol represented by formula 4A will be described by way of a specific example (compound in which $A_1$ is —$SCH_3$). In the phosphatidylinositol represented by the following formula, sulfur of $A_1$ forms a ring structure with a carbon-carbon bond of the inositol skeleton by phosphorylation. The sulfur of this ring structure has a positive charge. This ring structure is also extremely unstable, and has a property of easily forming a covalent bond with another compound.

[Chemical Formula 35]

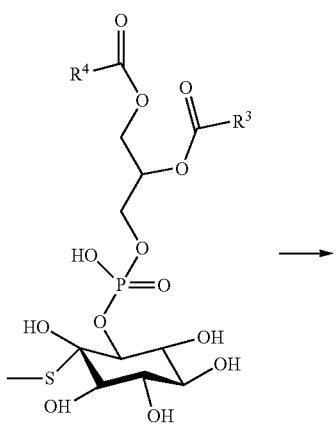

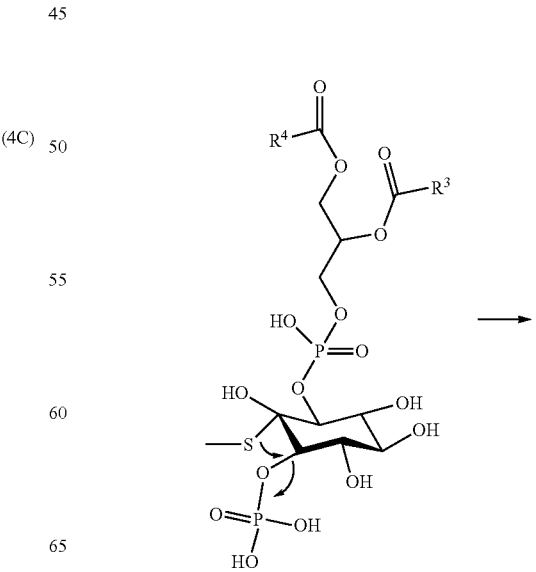

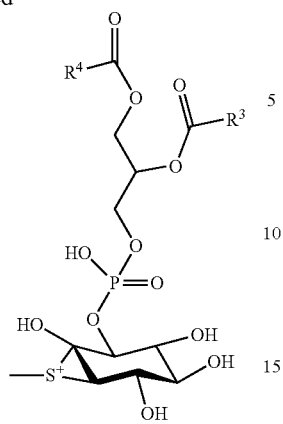

[Chemical Formula 36]

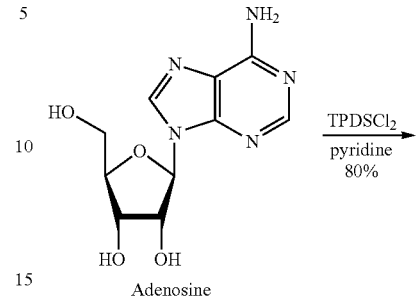

In a case where the β-modified phosphoric acid compound is phosphatidylinositol represented by formula 4A, in particular, the reaction of phosphoinositide-3-kinase (PI3K) is efficiently inhibited. PI3K generates phosphatidylinositol 3,4,5-trisphosphate by phosphorylating inositol phospholipids. These compounds are substances involved in a PI3K/Akt pathway, and the Akt is also an oncogene product. It is presumed that the phosphatidylinositol represented by formula 4A is phosphorylated, an active species represented by formula 4C is generated through the compound represented by formula 4B, and the active species covalently binds to PI3K, as a result of which the reaction is inhibited.

(4) Medicine

The phosphatidylinositol represented by formula 4A is an inhibitor of PI3K activity, and is useful as a therapeutic agent for a cancer, malignant lymphoma, leukemia, rheumatism, or the like.

(5) Method for Producing Phosphatidylinositol

As the method for producing phosphatidylinositol represented by formula 4A, a method similar to that for the nucleoside derivative represented by formula 2A can be used. That is, the phosphatidylinositol represented by formula 4A can be synthesized by the following procedure. First, hydroxyl groups other than the 2'-hydroxyl group of inositol are protected by using siloxanes as the protecting groups. Next, a trifluorosulfonic acid group is introduced at the 2'-position, and then the thioester is converted to a thiol group. Finally, the protecting groups are eliminated from the inositol.

EXAMPLES

Hereinafter, the present invention will be specifically described by way of Examples, but these Examples do not limit the object of the present invention. In addition, in the following Examples, the expression "%" is on a mass basis (mass percent) unless otherwise particularly specified.

The overall synthetic scheme of the nucleoside derivative in the following Examples is shown below. Hereinafter, the method for synthesizing a nucleoside derivative will be described according to the synthetic scheme (in addition, the numbers in the synthetic schemes are matched with the compound numbers). Further, the number of "%" means the yield.

[Chemical Formula 37]

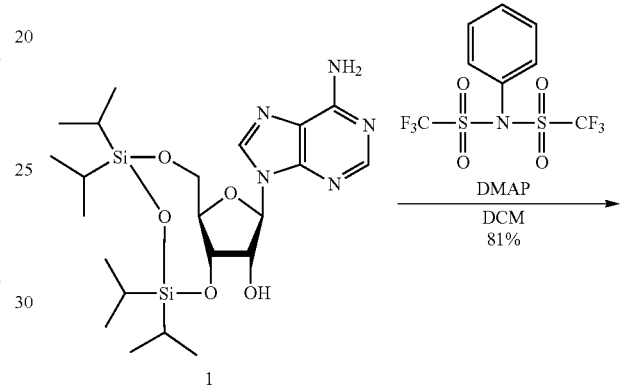

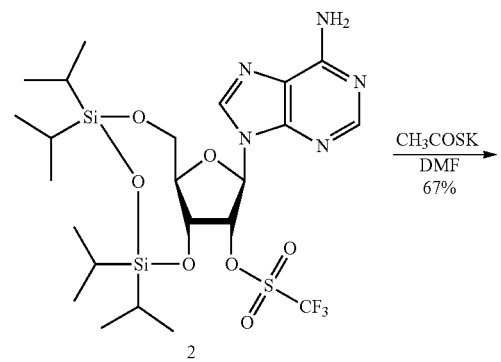

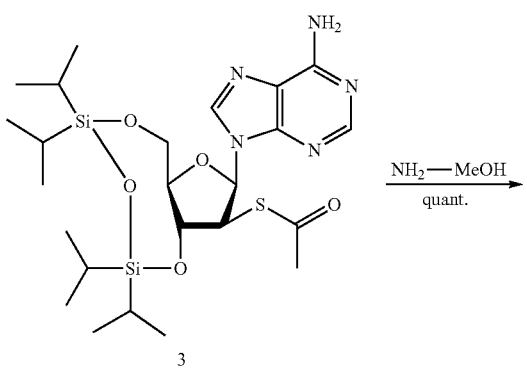

-continued
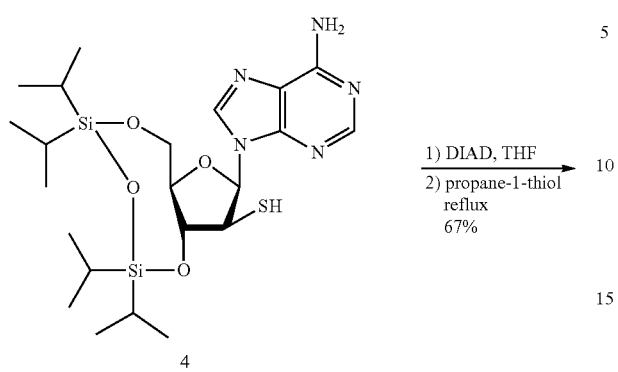
4
1) DIAD, THF
2) propane-1-thiol
reflux
67%
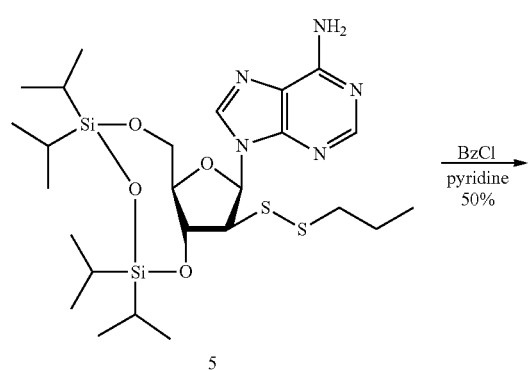
5
BzCl
pyridine
50%
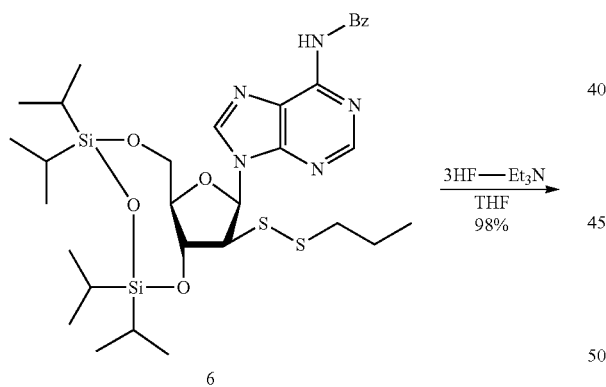
6
3HF—Et₃N
THF
98%
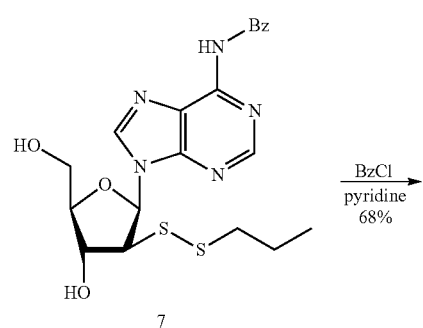
7
BzCl
pyridine
68%
-continued
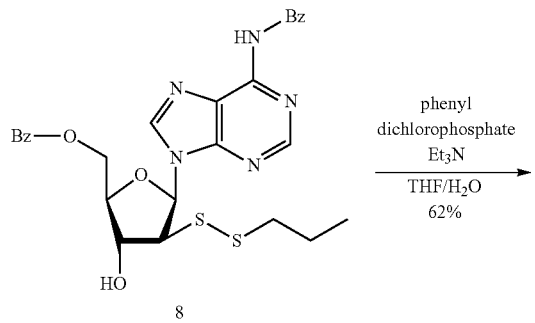
8
phenyl
dichlorophosphate
Et₃N
THF/H₂O
62%
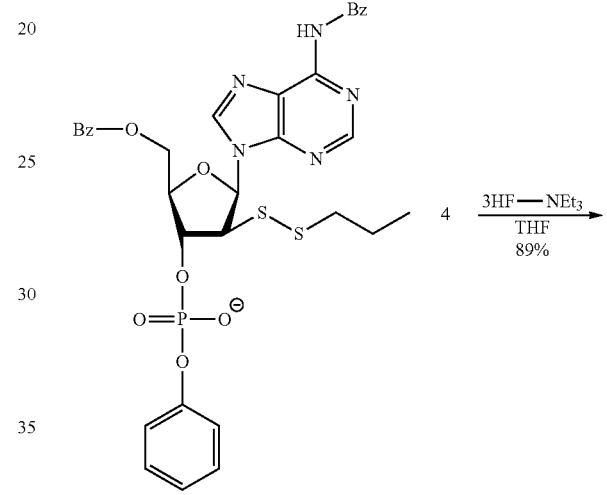
9
3HF—NEt₃
THF
89%
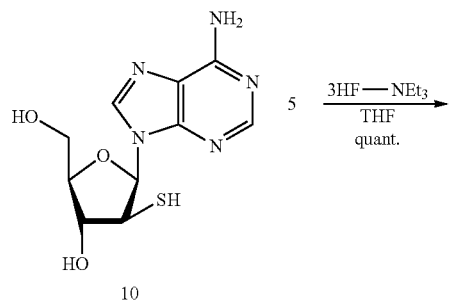
10
3HF—NEt₃
THF
quant.
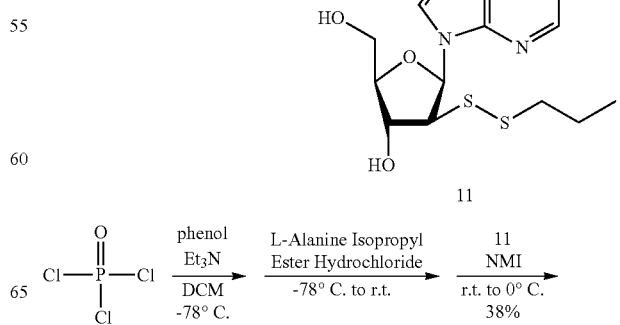
11
phenol
Et₃N
DCM
−78° C.
L-Alanine Isopropyl
Ester Hydrochloride
−78° C. to r.t.
11
NMI
r.t. to 0° C.
38%

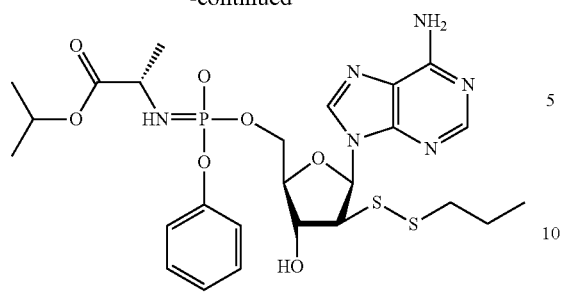

Pro A

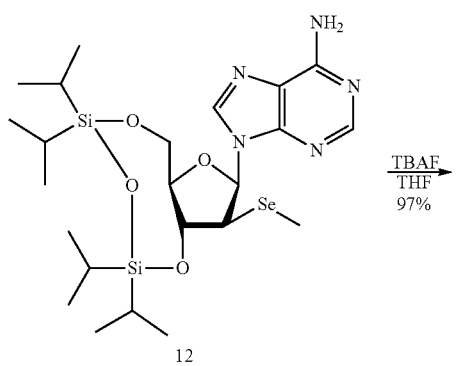

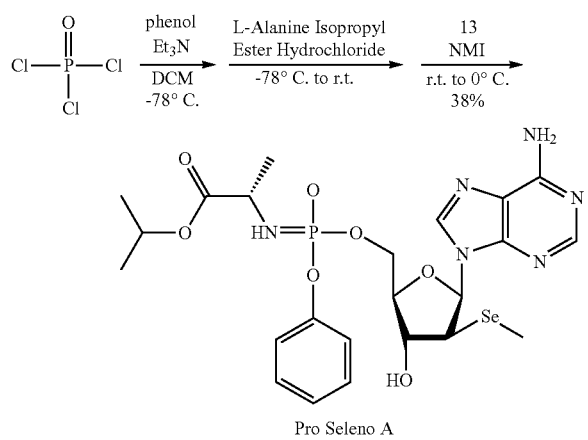

Pro Seleno A

1) POCl₃, PO(OMe)₃
   Bu₃N
2) (Bu₃N)₂P₂O₇H₄
   MeCN
3) NaClO₄, acetone
   43%

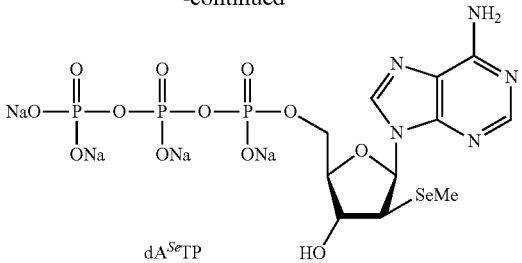

dA$^{Se}$TP

1. Synthesis of Nucleoside Derivative (1) Synthesis of Compound 1

Under an argon (Ar) atmosphere, adenosine (3.01 g, 10.1 mmol, 1.0 eq.) was dissolved in pyridine (65 mL) to obtain a mixture, TPDSCl₂ (3.2 mL, 10.1 mmol, 1.0 eq.) was added into the mixture, and the mixture thus obtained was stirred at room temperature for 46 hours. The solvent was distilled off under reduced pressure, and the resultant mixture was separated with ethyl acetate and water (0.1 M HCl aq., H₂O, sat. NaHCO₃ aq., brine). The drying was performed by the addition of anhydrous sodium sulfate, and then the filtration with a cotton plug was performed, subsequently the solvent was distilled off under reduced pressure. The residue was purified by neutral flash column chromatography (CHCl₃ (MeOH 0-4%)) to obtain compound 1 (4.14 g, 80%). The 1H-NMR information of the obtained compound is as follows.

¹H-NMR (400 MHz, CDCl₃): δ 1.06-1.13 (m, 28H), 3.31 (s, 1H), 4.01-4.16 (m, 3H), 4.56 (d, J=5.6 Hz, 1H), 5.07-5.11 (m, 1H), 5.79 (s, 2H), 5.97 (d, J=1.2 Hz, 1H), 7.97 (s, 1H), 8.28 (s, 1H).

(2) Synthesis of Compound 2

Under an Ar atmosphere, compound 1 (1.00 g, 1.83 mmol, 1.0 eq.) and DMAP (650 mg, 5.5 mmol, 3 eq.) were dissolved in dehydrated DCM (17 mL) under ice cooling to obtain a mixture, N-phenyltrifluoromethanesulfonimide (803 mg, 2.2 mmol, 1.2 eq.) was added into the mixture, and the mixture thus obtained was stirred for 2 hours. The resultant mixture was separated with ice-cooled dichloromethane and water (0.1 M AcOH aq., sat. NaHCO₃ aq., brine). The drying was performed by the addition of anhydrous sodium sulfate, and then the filtration with a cotton plug was performed, subsequently the solvent was distilled off under reduced pressure. The residue was purified by neutral flash column chromatography (hexane/ethyl acetate=1/1) to obtain compound 2 (946 mg, 81%). The ¹H-NMR information of the obtained compound is as follows. ¹H-NMR (400 MHz, CDCl₃): δ 1.06-1.11 (m, 28H), 4.02-4.20 (m, 3H), 5.26-5.29 (m, 1H), 5.72 (s, 2H), 5.78 (d, J=4.8 Hz, 1H), 6.10 (s, 1H), 7.96 (s, 1H), 8.26 (s, 1H).

(3) Synthesis of Compound 3

Under an Ar atmosphere, compound 2 (2.80 g, 4.36 mmol, 1.0 eq.) and potassium thioacetate (1.06 g, 9.28 mmol, 2.1 eq.) azeotroped with dehydrated acetonitrile were dissolved in dehydrated DMF (9 mL) to obtain a mixture, the mixture was stirred for 14.5 hours. The solvent was distilled off under reduced pressure, and the resultant mixture was separated with a hexane/ethyl acetate=1/5 mixed solvent and water (sat. NaHCO₃ aq., brine). The drying was performed by the addition of anhydrous sodium sulfate, and then the filtration with a cotton plug was performed, subsequently the solvent was distilled off under reduced pressure. The residue was purified by neutral flash column chromatography (hexane/ethyl acetate=2/3) to obtain compound 3 (1.72 g, 67%). The 1H-NMR information of the obtained compound is as follows.

$^1$H-NMR (400 MHz, CDCl$_3$): δ 1.01-1.18 (m, 28H), 2.15 (s, 3H), 3.97-4.03 (m, 2H), 4.23-4.27 (m, 1H), 4.54-4.58 (m, 1H), 5.01-5.06 (m, 1H), 6.12 (s, 1H), 6.40 (d, J=7.6 Hz, 1H), 7.90 (s, 1H), 8.23 (s, 1H).

(4) Synthesis of Compound 4

Under an Ar atmosphere, compound 3 (1.42 g, 2.50 mmol) was dissolved in 7 M NH$_3$—MeOH (25 mL) under ice cooling to obtain a mixture, the mixture was stirred for 1 hour. The solvent was distilled off under reduced pressure, and the resultant mixture was separated with ethyl acetate and water (sat. NaHCO$_3$ aq., brine). The drying was performed by the addition of anhydrous sodium sulfate, and then the filtration with a cotton plug was performed, subsequently the solvent was distilled off under reduced pressure to obtain compound 4 (1.75 g, quant.). The $^1$H-NMR information of the obtained compound is as follows. $^1$H-NMR (400 MHz, CDCl$_3$): δ 1.00-1.18 (m, 28H), 1.44 (d, J=8.4 Hz, 1H), 3.81-3.91 (m, 2H), 4.03-4.07 (m, 1H), 4.20-4.24 (m, 1H), 4.58-4.63 (m, 1H), 5.76 (s, 1H), 6.40 (d, J=7.6 Hz, 1H), 8.11 (s, 1H), 8.33 (s, 1H).

(5) Synthesis of Compound 5

Compound 4 (304 mg, 0.571 mmol, 1.0 eq.) was dissolved in THF (1.9 mL, 0.3 M to compound 4) to obtain a mixture, DIAD (124 μL, 0.628 mmol, 1.1 eq.) was added into the mixture, and the mixture thus obtained was stirred for 18 hours. Into the resultant mixture, 1-propanethiol (3.1 mL, 33.7 mmol, 59 eq.) was added, and the obtained mixture was heated to 80° C. and stirred for 29 hours, and then cooled to room temperature. The solvent was distilled off under reduced pressure, and the residue was purified by neutral flash column chromatography (hexane/ethyl acetate=1/1) to obtain compound 5 (230 mg, 67%). The 1H-NMR information of the obtained compound is as follows.

$^1$H-NMR (400 MHz, CDCl$_3$): δ 0.88-0.92 (m, 3H), 1.06-1.17 (m, 28H), 1.53-1.58 (m, 2H), 2.53 (t, J=14.4 Hz, 2H), 3.88-3.94 (m, 2H), 4.01-4.05 (m, 1H), 4.15-4.20 (m, 1H), 4.74 (t, J=9.2 Hz, 1H), 5.68 (s, 1H), 6.49 (d, J=7.2 Hz, 1H), 7.97 (s, 1H), 8.32 (s, 1H).

(6) Synthesis of Compound 6

Under an Ar atmosphere, compound 5 (314 mg, 0.523 mmol, 1.0 eq.) was dissolved in pyridine (2.1 mL, 0.25 M to compound 5) under ice cooling to obtain a mixture, and BzCl (91 μL, 0.785 mmol, 1.5 eq.) was added into the mixture, and the mixture thus obtained was stirred for 3 hours and 30 minutes. Into the resultant mixture, BzCl (60 μL, 0.523 mmol, 1.0 eq.) was added, and the obtained mixture was further stirred for 1 hour. Into the stirred mixture, BzCl (30 μL, 0.262 mmol, 0.5 eq.) was added, and the mixture thus obtained was further stirred for 40 minutes. Into the resultant mixture, BzCl (60 μL, 0.523 mmol, 1.0 eq.) was added, and the obtained mixture was further stirred for 40 minutes. Into the stirred mixture, 4 mL of water was added, the mixture thus obtained was stirred for 5 minutes, and then into the stirred mixture, 8 mL of 28% ammonia aqueous solution was added, the obtained mixture was stirred for 15 minutes. The resultant mixture was separated with ethyl acetate and water (sat. NaHCO$_3$ aq., brine). The drying was performed by the addition of anhydrous sodium sulfate, and then the filtration with a cotton plug was performed, and the solvent was distilled off under reduced pressure. The residue was purified by neutral flash column chromatography (hexane/ethyl acetate=1/1) to obtain compound 6 (183 mg, 50%). The $^1$H-NMR information of the obtained compound is as follows.

$^1$H-NMR (400 MHz, CDCl$_3$): δ 0.88-0.92 (m, 3H), 1.01-1.18 (m, 28H), 1.55-1.61 (m, 2H), 2.57 (t, J=15.2 Hz, 2H), 3.91-3.97 (m, 2H), 4.03-4.07 (m, 1H), 4.18-4.22 (m, 1H), 4.74 (t, J=9.2 Hz, 1H), 6.57 (d, J=7.2 Hz, 1H), 7.52 (t, J=8.0 Hz, 2H), 7.61 (t, J=7.2 Hz, 2H), 8.02 (d, J=7.2 Hz, 1H), 8.16 (s, 1H), 8.80 (s, 1H), 9.08 (s, 1H); $^{13}$C-NMR (100 MHz, CDCl$_3$): δ 12.5, 12.9, 13.0, 13.1, 13.6, 17.1, 17.4, 17.5, 22.1, 41.3, 61.7, 63.3, 73.9, 83.9, 84.8, 123.0, 127.9, 128.9, 132.8, 133.9, 142.0, 149.6, 151.6, 152.6, 164.7; HRMS (ESI$^+$) calc. m/z 704.28 (M+H$^+$), 726.26 (M+Na$^+$), found m/z 704.2821 (M+H$^+$), 726.2623 (M+Na$^+$).

(7) Synthesis of Compound 7

Under an Ar atmosphere, compound 6 (241 mg, 0.342 mmol, 1.0 eq.) was dissolved in THF (3.4 mL) to obtain a mixture, 3HF-Et$_3$N (139 μL, 0.855 mmol, 2.5 eq.) was added into the mixture, and the mixture thus obtained was stirred for 2 hours and 20 minutes. The solvent was distilled off under reduced pressure, and the residue was purified by neutral flash column chromatography (CHCl$_3$ (MeOH 0-5%)) to obtain compound 7 (154 mg, 98%). The $^1$H-NMR information of the obtained compound is as follows.

$^1$H-NMR (400 MHz, CD$_3$SOCD$_3$): δ 0.78-0.81 (m, 3H), 1.40-1.45 (m, 2H), 2.49-2.55 (m, 2H), 3.66-3.77 (m, 2H), 3.82-3.84 (m, 1H), 3.96-3.99 (m, 1H), 4.41-4.45 (m, 1H), 5.14 (t, J=3.6 Hz, 1H), 5.92 (d, J=4.4 Hz, 1H), 6.66 (d, J=4.8 Hz, 1H), 7.55 (t, J=8.0 Hz, 1H), 7.64 (t, J=7.6 Hz, 1H), 8.03 (d, J=7.2 Hz, 1H), 8.64 (s, 1H), 8.74 (s, 1H), 11.21 (br, 1H); $^{13}$C-NMR (100 MHz, CD$_3$OD): δ 13.1, 22.9, 41.9, 61.2, 63.2, 72.8, 86.0, 86.4, 124.6, 129.4, 129.7, 133.8, 134.9, 144.8, 151.0, 153.1, 153.3, 168.0; HRMS (ESI$^+$) calc. m/z 462.13 (M+H$^+$), 484.11 (M+Na$^+$), found m/z 462.1288 (M+H$^+$), 484.111 (M+Na$^+$).

(8) Synthesis of Compound 8

Under an argon atmosphere, SM (154 mg, 0.344 mmol, 1.0 eq.) was dissolved in pyridine (3.4 ml, 0.1 M to compound 7) at 0° C. to obtain a mixture, and BzCl (46 μL, 0.401 mmol, 1.2 eq.) was added into the mixture while stirring. Into the resultant mixture, while tracking the reaction by TLC, 0.6 eq., 0.6 eq., 1.2 eq., and 1.2 eq. of BzCl were added after the lapse of 2 hours, 4 hours, 7 hours, and 10 hours from the start of the stirring, and into the mixture thus obtained, MeOH (5 ml) was added after the lapse of 11 hours from the start of the reaction, and the obtained mixture was stirred for 10 min. The solvent was distilled off under reduced pressure, and the resultant mixture was separated with ethyl acetate (EtOAc) and water (sat. NaHCO$_3$ aq., brine). After the drying was performed with salt cake (sodium sulfate), the solvent was distilled off, and the residue was purified by neutral flash column (H/A=1/1) to obtain compound 8 (133 mg, 68%). The $^1$H-NMR information of the obtained compound is as follows.

$^1$H-NMR (400 MHz, CDCl$_3$): δ 0.738 (t, J=7.2 Hz, 3H), 1.38 (m, 2H), 2.42 (m, 2H), 3.96 (t, J=7.6 Hz, 1H), 4.30 (m, 1H), 4.70-4.72 (m, 2H), 4.82 (t, J=7.6 Hz, 1H), 5.44 (brs, 1H), 6.59 (d, J=7.2 Hz, 1H), 7.37-7.50 (m, 6H), 7.97-8.00 (m, 4H), 8.15 (s, 1H), 8.71 (s, 1H), 9.51 (brs, 1H); $^{13}$C-NMR (100 MHz, CDCl$_3$): δ 12.8, 14.2, 21.1, 21.9, 41.1, 60.5, 61.3, 63.8, 74.4, 82.3, 85.5, 122.7, 128.0, 128.5, 128.8, 129.4, 129.7, 129.8, 132.8, 133.4, 133.6, 142.2, 149.5, 151.3, 152.6, 165.0, 166.5, 171.3; HRMS (ESI$^+$) calc. m/z 566.15 (M+H$^+$), 588.14 (M+Na$^+$), 604.11 (M+K$^+$), found m/z 544.1461 (M+H$^+$), 588.1327 (M+Na$^+$), 604.1017 (M+K$^+$).

(9) Synthesis of Compound 9 (β-Modified Phosphoric Acid Compound)

Under an Ar atmosphere, phenylphosphorodichloride (9 μL, 0.06 mmol, 1.5 eq. in 150 μL THF), dehydrated TEA (28 μL, 0.2 mmol, 5.0 eq. in 150 μL THF), and compound 8 (23 mg, 0.04 mmol, 1.0 eq. in 200 μL THF and 28 μL TEA) were added at 0° C. to obtain a mixture, the mixture was stirred for 1.5 h, and then the reaction system was returned to room temperature, and the mixture was stirred for 2.5 h. After that, into the resultant mixture, 150 μL of MQ was added, and the obtained mixture was stirred overnight, and then the stirred mixture was purified by high-performance liquid chromatography (HPLC). The reaction yield was 62% as calculated by HPLC. HRMS (ESI$^-$) calc. m/z 720.14 (M$^-$), found m/z 719.7807 (M$^-$), HRMS (ESI$^+$) calc. m/z 722.15 (M+H$^+$), found m/z 722.1443 (M+H$^+$).

(10) Synthesis of Compound 10 (β-Modified Phosphoric Acid Compound Precursor A-1)

Under an Ar atmosphere, compound 4 (549 mg, 1.04 mmol, 1.0 eq.) was dissolved in THF (10 mL) to obtain a mixture, 3HF-Et$_3$N (424 μL, 2.6 mmol, 2.5 eq.) was added into the mixture, and the mixture thus obtained was stirred for 2 hours and 40 minutes. The solvent was distilled off under reduced pressure, the suction filtration was performed with DCM, the washing was performed, and as a result of which compound 10 (266 mg, 89%) was obtained. The 1H-NMR information of the obtained compound is as follows.

$^1$H-NMR (400 MHz, CD$_3$SOCD$_3$): δ 3.31-3.39 (m, 2H), 3.73-3.76 (m, 4H), 4.24-4.29 (m, 1H), 5.78 (d, J=6.0 Hz, 1H), 6.36 (d, J=7.6 Hz, 1H), 7.29 (s, 2H), 8.12 (s, 1H), 8.30 (s, 1H).

(11) Synthesis of Compound 11 (β-Modified Phosphoric Acid Compound Precursor A-2)

Under an Ar atmosphere, compound 5 (553 mg, 0.920 mmol, 1.0 eq.) was dissolved in THF (9.2 mL) to obtain a mixture, 3HF-Et$_3$N (375 μL, 2.30 mmol, 2.5 eq.) was added into the mixture, and the mixture thus obtained was stirred for 2 hours. The solvent was distilled off under reduced pressure, and the residue was purified by neutral flash column chromatography (CHCl$_3$ (MeOH 0-5%)) to obtain compound 11 (337 mg, quant.). The 1H-NMR information of the obtained compound is as follows.

$^1$H-NMR (400 MHz, CD$_3$OD): δ 0.74-0.78 (m, 3H), 1.36-1.43 (m, 2H), 2.44-2.47 (m, 2H), 3.84-3.91 (m, 4H), 4.51 (t, J=8.8 Hz, 1H), 6.54 (d, J=7.2 Hz, 1H), 8.16 (s, 1H), 8.32 (s, 1H).

(12) Synthesis of Pro A

A solution of phenol (132 mg, 1.4 mmol, 1.0 eq.) and triethylamine (132 mg) was added into a solution of phosphoryl chloride (130 μL, 1.4 mmol, 1.0 eq.) in anhydrous DCM (4.2 ml) to obtain a mixture, at −78° C. Into the mixture, a solution of 195 μL, 1.4 mmol, 1.0 eq.) in anhydrous DCM (1.4 ml) was added dropwise. The mixture thus obtained was stirred at the same temperature for 3 hours, and then the reaction mixture was treated with a L-alanine isopropyl ester hydrochloride (235 mg, 1.4 mmol, 1.0 eq.) at one time, subsequently, into the resultant mixture, triethylamine (390 μL, 2.8 mmol, 2.0 eq.) was added dropwise. The obtained mixture was further stirred at −78° C. for 1 hour, and then warmed to room temperature over 1 hour. The warmed mixture was cooled to 0° C., and then the mixture was further treated with a solution of compound 11 (94.2 mg, 0.280 mmol, 0.2 equivalents) in anhydrous DCM (1.4 ml) and N-methyl imidazole (NMI, 111 μL, 1.4 mmol, 1.0 equivalent), and the treated mixture was stirred at 0° C. for 16 hours. The reaction mixture was treated with H$_2$O (7.0 ml), and the treated mixture was subjected to extraction with DCM. The organic layer was washed sequentially with 0.5 M dilute HCl and saline. The washed organic layer was dried over anhydrous Na$_2$SO$_4$, and then the dried organic layer was concentrated, subsequently, the concentrated organic layer was purified by silica gel column chromatography (DCM/MeOH=−10/1) and HPLC to obtain a desired product Pro A (48 mg, 38%). The NMR information of the obtained compound is as follows.

$^1$H-NMR (400 MHz, DMSO): δ −0.06 (t, J=7.6 Hz, 3H), 0.18 (d, J=6.4 Hz, 2H), 0.23-0.27 (m, 4H), 0.30 (d, J=6.8 Hz, 3H), 0.49-0.59 (m, 2H), 1.64-1.66 (m, 2H), 2.78-2.91 (m, 1H), 3.06-3.13 (m, 2H), 3.36-3.50 (m, 2H), 3.64-3.70 (m, 1H), 3.83-3.89 (m, 1H), 5.08-5.21 (m, 2H), 5.68 (d, J=8.0 Hz, 1H), 6.29-6.33 (m, 3H), 6.45-6.49 (m, 4H), 7.28 (s, 1H), 7.35 (s, 1H); $^{13}$C-NMR (100 MHz, DMSO): δ 12.5, 19.6, 21.2, 21.3, 49.7, 62.4, 67.8, 72.6, 83.6, 118.8, 120.0, 120.1, 124.4, 129.5, 140.0, 149.0, 150.7, 152.5, 156.0, 172.5; $^{31}$P-NMR (162 MHz, CDCl$_3$): δ 4.27 (P(R)), 4.67 (P(S)); HRMS (ESI$^+$) calc. m/z 627.18 (M+H$^+$), 649.16 (M+Na$^+$), 665.14 (M+K$^+$), found m/z 627.1786 (M+H$^+$), 649.1611 (M+Na$^+$), 665.1328 (M+K$^+$).

(13) Synthesis of Compound 12 (β-Modified Phosphoric Acid Compound Precursor (Selenium))

Under ice cooling, sodium borohydride (289 mg, 7.64 mmol) was added to obtain a reaction mixture into ethanol (5 mL) in which dimethyldiselenide (300 μL, 3.17 mmol) had been dissolved. Compound 2 (3.36 g, 5.30 mmol) was dissolved in THF (20 mL) to obtain a mixture, the mixture was added into the reaction mixture, and the mixture thus obtained was stirred at 70° C. for 3.5 hours. Into the resultant mixture, dimethyldiselenide (100 μL, 1.06 mmol) and sodium borohydride (62.3 mg, 1.64 mmol) were added, and the obtained mixture was stirred at 60° C. for 2.5 hours. The stirred mixture was neutralized with 1 M hydrochloric acid, and then the solvent was distilled off. The residue was dissolved in ethyl acetate (50 mL), the mixture was washed with water three times and with brine once, and the organic layer was dried over salt cake. The solvent was distilled off, and then the residue was purified by neutral flash column chromatography (hexane/ethyl acetate=1/1→9/1→ethyl acetate/methanol=9/1) to obtain compound 12 (1.90 g, 61%). A pressure container was used for the present reaction. The $^1$H-NMR information of the obtained compound is as follows. $^1$H-NMR (400 MHz, CDCl$_3$): δ 0.89-1.22 (m, 28H), 1.95 (s, 3H), 3.72-3.90 (m, 2H), 4.04-4.23 (m, 2H), 4.73 (dd, J=8.4 Hz, 10.4 Hz, 1H), 5.64 (br, s, 2H), 6.49 (d, J=7.6 Hz, 1H), 8.26 (s, 1H); $^{13}$C-NMR (100 MHz, DMSO): δ 5.801, 12.70, 13.15, 13.16, 13.86, 17.13, 17.21, 17.25, 17.27, 17.48, 17.51, 17.57, 17.64, 49.87, 61.23, 74.94, 84.23, 84.58, 119.56, 139.32, 149.93, 152.754; HRMS (ESI$^+$) calc. m/z 588.19 (M+H$^+$), 610.18 (M+Na$^+$), found m/z 588.1945 (M+H$^+$), 610.1768 (M+Na$^+$).

(14) Synthesis of Compound 13 (SelenoA: β-Modified Phosphoric Acid Compound Precursor (Selenium))

Compound 12 (1.83 g, 3.12 mmol) was dissolved in THF (18 mL) under ice cooling to obtain a mixture, TBAF (1 M in THF, 7.8 mL, 7.80 mmol) was added into the mixture, and the mixture thus obtained was stirred for 17.5 hours. The solvent was distilled off, and the residue was purified by neutral flash column chromatography (dichloromethane/methanol=95/5→85/15) to obtain compound 13 (1.04 g, 97%). The $^1$H-NMR information of the obtained compound is as follows.

$^1$H-NMR (400 MHz, DMSO-d6): δ 1.85 (s, 3H), 3.64-3.83 (m, 4H), 4.43 (m, 1H), 5.73 (dd, J=4.0 Hz, 6.0 Hz, 1H), 6.45 (dd, J=3.6 Hz, 7.6 Hz, 1H), 7.28 (s, 2H), 8.28 (s, 1H);

$^{13}$C-NMR (100 MHz, DMSO): δ 4.17, 49.1, 59.8, 73.3, 84.1, 85.0, 118.3, 139.3, 149.2, 152.5, 156.0; HRMS (ESI$^+$) calc. m/z 346.04 (M+H$^+$), 368.02 (M+Na$^+$), found m/z 346.0402 (M+H$^+$), 368.0214 (M+Na$^+$).

(15) Synthesis of Pro SelenoA

POCl$_3$ (134 μL, 1.50 mmol) was dissolved in dichloromethane (4.5 mL) to obtain a mixture, and the mixture was stirred at −78° C. Phenol (132.6 mg, 1.46 mmol) and triethylamine (201 uL, 1.50 mmol) were dissolved in dichloromethane (1.5 mL) to obtain a mixture, the mixture was added dropwise into the above stirred mixture, and the resultant mixture was stirred for 3 hours. Into the stirred mixture, an L-isopropylalanine hydrochloride (248.4 mg, 1.54 mmol) and triethylamine (201 uL, 3.00 mmol) were added, the mixture thus obtained was further stirred for 1 hour, and the stirred mixture was heated to room temperature. Compound 13 (94.2 mg, 0.27 mmol) and NMI (114 uL, 1.50 mmol) were dissolved in dichloromethane (1.5 mL) to obtain a mixture, and the mixture was added dropwise into the above heated mixture. The resultant mixture was stirred at 0° C. for 20.5 hours, and then the reaction was quenched with water. The purification was performed by reverse-phase high-performance liquid chromatography (RP-HPLC, MiliQ/ACN=20/80→50/50) to obtain Pro SelenoA (33.5 mg, 19%). The NMR information of the obtained compound is as follows.

$^1$H-NMR (400 MHz, CD$_2$Cl$_2$): δ 1.01-1.25 (m, 9H), 1.88 (s, 3H), 3.64-3.89 (m, 3H), 4.20-4.83 (4 m, H), 5.82-6.04 (m, 2H), 6.45 (d, 1H), 7.05-7.43 (m, 7H), 8.13 (d, 2H); $^{13}$C-NMR (100 MHz, CD$_2$Cl$_2$): δ 4.95, 20.24, 21.84, 48.93, 50.26, 66.50, 79.71, 83.39, 84.81, 119.2, 120.7, 125.0, 130.1, 140.1, 149.5, 151.2, 153.0, 156.6, 173.1; HRMS (ESI$^+$) calc. m/z 615.11 (M+H$^+$), found m/z 615.1244 (M+H$^+$);

(16) Synthesis of dA$^{Se}$TP

Seleno adenosine (compound 13: 101 mg, 0.30 mmol) and tributylamine (643 μL, 2.70 mmol) were added into trimethyl phosphate (84.1 mg) to obtain a mixture, and into the mixture, phosphoryl chloride (84 μL, 0.90 mmol) was added dropwise while stirring at −30° C., and then the resultant mixture was stirred for 16 hours. Bis(tributylammonium)pyrophosphate (993.5 mg, 1.51 mmol) and tributylamine (600 μL) were added into acetonitrile (1.6 mL) to obtain a mixture, and the mixture was stirred for 24 hours. Into the stirred mixture, 1 M TEAB (5 mL) was added, and the mixture thus obtained was lyophilized. The progress of the reaction was analyzed by HPLC (DEAE-2SW, 1 M ammonium formate/MQ=0/100→50/50), and the purification was performed by HPLC (C18 Hydrosphere, 50 mM TEAB/ACN=100/0→70/30) to obtain a triethylammonium salt of triphosphate. Into the obtained triethylammonium salt, a solution of 0.1 M sodium perchlorate in acetone was added, and a sodium salt (93.9 mg, 43%) of triphosphate was obtained by suction filtration. The NMR information of the obtained compound is as follows.

$^1$H-NMR (400 MHz, D$_2$O): δ 8.28 (s, 1H), 8.03 (s, 1H), 6.40 (d, J=8 MHz, 1H), 4.42 (t, J=10 MHz, 1H), 4.23 (d, J=1.6 MHz, 2H), 3.98 (m, 1H), 3, 74 (q, J=7.2 MHz, 1H), 1.64 (s, 3H); $^{13}$C-NMR (100 MHz, D$_2$O): δ 4.26, 48.19, 63.43, 71.78, 82.69, 85.85, 118.1, 140.6, 148.6, 152.7, 155.6; $^{31}$P-NMR (160 MHz, D$_2$O): δ −5.39 (br, 1P), −10.28 (d, J=17 MHz, 1P), −20.81 (br, 1P); HRMS (ESI$^−$) calc. m/z 583.92 (M−H)$^−$, found m/z 583.9202 (M−H)$^−$;

2. Chain Cleavage Reaction

A solution of compound 9 (MeCN: H$_2$O=2: 1, 35 mM, 100 uL), HEPES Buffer (50 uL, pH=9.0, 500 mM), H$_2$O (332.5 uL), and a dithiothreitol (DTT) aqueous solution (1 M, 17.5 uL) were mixed to obtain a mixture, and then the mixture was incubated at 25° C. for 20 hours. The incubated mixture was analyzed by HPLC (under the conditions described below), and the peaks were identified by high resolution mass spectrometry (HRMS)-electrospray ionization (ESI). A graph of the results is shown in FIG. 2.

<HPLC Conditions>

Column: Hydrosphere C18 250×4.6 mm S-5 μm 12 nm

Eluent: A) 50 mM TEAA buffer, 5% ACN

B) ACN

Gradient: B conc. 0-10% (0-10 min), 10-100% (10-22.5 min), 100% (22.5-30 min)

Flow rate: 1 mL/min, Detection: 260 nm

From the results of HPLC in FIG. 2, a peak of a nucleoside derivative (compound A) and a peak of a phenyl phosphate (compound B) were confirmed. According to this confirmation, it was confirmed that if a disulfide group at the 2'-position was deprotected by DTT in a state that the 3'-position of ribose was phosphorylated, the phosphoric acid moiety at the 3'-position was cleaved by the following reaction, and decomposition into an activated nucleoside derivative having a thiirane structure and a phenyl phosphate was generated.

[Chemical Formula 38]

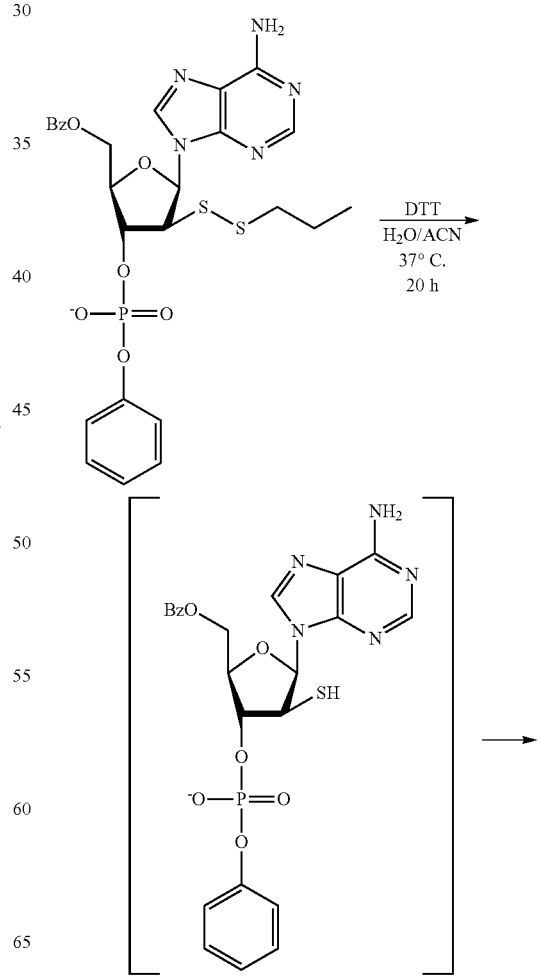

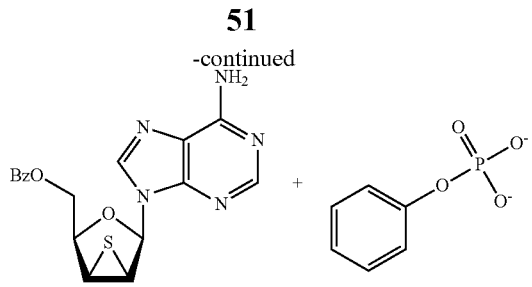

3. Antiproliferative Effect of Hepatitis B Virus (HBV)

A cell line EB-HBCe, which is derived from a human liver cancer cell HuH-7 and in which the HBV genome (genotype C) constantly replicates, was plated in a 24-well plate, compound A-1 (compound 10) and compound A-2 (compound 11) were added at a final concentration of 10 or 100 µM into the plate, and the cell line EB-HBCe was cultured for 9 days. During the culture, the medium was replaced with new one and the above compounds were added at the same concentration into the plate, every three days. The total RNA was extracted from the cultured cells with TRI Reagent (Molecular Research Center, Inc.), and treated with deoxyribonuclease I (DNase I) and ribonuclease (RNase) inhibitors. By SuperScript VILO cDNA synthesis kit (Invitrogen), cDNA was synthesized, and viral RNA (pgRNA), which was a HBV replicative intermediate, was quantified by a quantitative polymerase chain reaction (PCR) using SYBR qPCR Mix Kit (TOYOBO CO., LTD.). The results are shown in FIG. 3. The results of addition of control, 10 µM of compound A-1, 100 µM of compound A-1, 10 µM of compound A-2, and 100 µM of compound A-2 are shown in order from the left side of the graph. Further, the result of addition of 10 µM of entecavir (ETV) being a therapeutic agent for hepatitis is shown on the rightmost side.

From FIG. 3, it was indicated that the viral RNA was decreased in a case where both compound A-1 and compound A-2 were added each at 100 µM. Therefore, it was found that all of the compounds can suppress the proliferation of hepatitis B virus. In particular, when comparing the results of compound A-1 and compound A-2 each at a concentration of 100 µM with each other, the amount of viral RNA was slightly lower in compound A-2 than that in compound A-1. From these results, it was found that compound A-2 had a higher antiproliferative effect of virus than that of compound A-1 when compared at the same concentration.

4. Irreversible Inhibition Experiment

Into a solution containing the following template RNA (0.2 µM, final concentration, the same applies hereinafter), the following primer DNA (0.2 µM), dCTP, dGTP, and dTTP (each 100 µM), Tris-HCl (pH 8.3, 5 mM), KCl (5 mM), DTT (0.2 mM), and MgCl2 (0.5 mM), 0.25 µL of AMV reverse transcriptase (20 U/µL), and dATP or ddATP or dASeTP (100 µM) were added to obtain a mixture, and the mixture was incubated at 42° C. for 3 hours. The resultant mixture was subjected to ultrafiltration 3 times by using Microcon 100K, and then the protein solution was concentrated by using Amicon 3K. By using the protein solution, the chain extension reaction was performed again (template RNA 0.2 µM, primer DNA 0.2 µM, 100 µM each dNTP, Tris-HCl (pH 8.3) 2.5 mM, KCl 5 mM, DTT 0.2 mM, 0.5 mM MgCl$_2$, AMV reverse transcriptase 0.1 U/µL).

At 5 minutes, 30 minutes, and 60 minutes of the reaction time, 10 µL of sample was taken out and added to 2× denaturing buffer, and the reaction was terminated. Each sample was subjected to electrophoresis with 20% dPAGE (7.5 M Urea, 1×TBE, 7.5% formamide, 20 mA const.), and the extended nucleic acid was quantitatively detected by fluorescence emission. The results are shown in FIG. 4.

Primer DNA: 5'-(FAM)-GGTGGACTTTCGC-3' (SEQ ID NO. 1)

Template RNA: 5'-ACGACGUGCGAAAGUCCACC-3' (SEQ ID NO. 2)

From FIG. 4, it was found that dA$^{Se}$TP inhibited the nucleic acid extension reaction by a reverse transcriptase.

5. Anti-HBV Activity

A cell line EB-HBCe, which is derived from a human liver cancer cell HuH-7 and in which the HBV genome (genotype C) constantly replicates, was plated in a 24-well plate, respective compound were added at various final concentrations into the plate, and the cell line EB-HBCe was cultured for 9 days. During the culture, the medium was replaced with new one and the above compounds were added at the same concentration into the plate, every three days.

The culture supernatant was collected, the viral particles were precipitated by the addition of a PNE solution (8.45% PEG 6000, 0.445 M NaCl, 13 mM EDTA), and then the nucleic acids outside the particles were removed by the treatment with DNase I (TAKARA BIO INC.) and RNase A (TAKARA BIO INC.) at 37° C. for 1 hour. Further, after the overnight treatment with Proteinase K, the DNA was extracted with phenol/chloroform, and precipitated with ethanol. The precipitate was solubilized, and then the HBV DNA was quantitatively measured by using SYBR qPCR Mix Kit (TOYOBO CO., LTD.). The results are shown in FIG. 5. In FIG. 5, the "SelenoA" indicates the results of addition of compound 13, and the "entecavir" indicates the result of addition of entecavir.

From FIG. 5, it was found that all of SelenoA (compound 13), Pro SelenoA, and Pro A showed anti-HBV activity, and as the concentration of addition was higher, the activity became higher. In particular, it was found that Pro SelenoA showed the highest anti-HBV activity among these three kinds at the concentration of addition of 10 µM.

7. Anti-HIV Activity (1) Anti-HIV Activity Measurement

TZM-bl cells were cultured in a medium in which fetal bovine serum (Japan Bio Serum) having a final concentration of 10% had been added into Dulbecco's modified Eagle's Medium (DMEM) (SIGMA/Cat. No. D5796), under the conditions of 37° C. and 5% CO$_2$. TZM-bl cells were plated in a 96-well microplate (1.3×10$^4$ cells/100 µL DMEM+10% FBS). On the following day, a drug solution, and HIV-1 (NL4-3, 10 ng) were added to the culture medium in this order. After two days, 200 µL of culture supernatant was removed, 100 µL of 1×Steady Glo (Promega/Cat. No. E2510) was added into the resultant medium, luciferase in 80 µL of scraped cell lysate was quantified with a dedicated plate (Coster/Cat. No. 3912) IESEL, VERITAS Microplate Luminometer (Promega), and the anti-HIV-1 activity (EC$_{50}$) of the drug was calculated. Experiments were performed on multiple compounds by using various types of viruses. The results are shown in the following Table (A). In Table (A), the "AZT" means azidothymidine, the "Lamivudine" means lamivudine, and the "Didanosine" means didanosine.

(2) Cytotoxicity Evaluation

In MTT assay, Celltiter 96 Non-radioactive Cell Proliferation Assay (Promega) was used. MT-4 cells were infected with HIV-1 NL4-3 at multiplicity of infection (MOI)=0.001. HIV-1-infected (37° C., 1-1.5 hours) or -uninfected MT-4 cells (2.5×10$^5$/ml, 100 µL) were aliquoted into a 96-well microplate (final DMSO concentration: 0.5%), and the culture was started at 37° C. and 5% $CO_2$. On the 5th day of the culture, the culture supernatant (100 µL) was removed, 15 µL of dye solution (MTT reagent) was added into each well, and the cells were cultured in a $CO_2$ incubator for 1 hour. Subsequently, 100 µL of solubilization solution/stop mix was added into each well, mixed sufficiently, and the obtained mixture was left to stand at 4° C. overnight. After returning the temperature of the plate to room temperature, DD570/690 was measured with a spectrophotometer (BIO-TEK ELx808, $CC_{50}$). The results are shown in the following Table (B).

TABLE 1

(A) $EC_{50}$ for HIV

| Virus Types | AZT | Lamivudine | Didanosine | Pro Seleno A |
|---|---|---|---|---|
| WT | 0.042 | 1.2 | 3.2 | 0.98 |
| M184V | 0.033 | >100 | 8.3 | 2.0 |
| M41L/T215Y | 0.12 | 1.7 | 5.6 | 1.3 |
| M41L/T69SSG/T215Y | 18 | 24 | 17 | 1.4 |

(B) CC50

| AZT | Pro Seleno A |
|---|---|
| 45 | >100 |

(µM)

In Table 1, from the results of (A), Pro SelenoA showed higher anti-HIV activity as compared with Lamivudine, and Didanosine. Further, with respect to HIV-type M41L/T69SSG/T215Y, Pro SelenoA showed more excellent anti-HIV activity as compared with AZT. In addition, from the results of (B), it was found that the toxicity was lower in ProSelenoA than that in AZT.

The invention claimed is:

1. A β-modified phosphoric acid compound precursor comprising
a structure represented by the following formula 3A,
[Chemical Formula 3A]

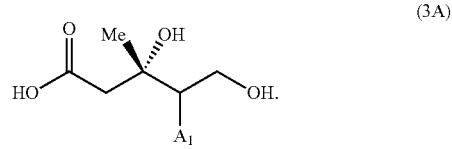

(3A)

wherein $A_1$ represents —$SR_1$, —S—S—$R_1$, —$SeR_1$, or —X, where X is a halogen selected from the group consisting of fluoro, chloro, bromo, and iodo; and $R_1$ represents hydrogen, an alkyl group having 1 to 20 carbon atoms, an aryl group having 1 to 20 carbon atoms, or an alkenyl group having 1 to 20 carbon atoms.

2. A reaction inhibitor comprising the β-modified phosphoric acid compound precursor according to claim 1.

3. A pharmaceutical composition, comprising the reaction inhibitor according to claim 2.

4. A method for inhibiting a phosphorylation reaction by the reaction inhibitor according to claim 2, comprising:
preparing a β-modified phosphoric acid compound precursor represented by formula 3A; and
generating a β-modified phosphoric acid compound represented by the following formula 3B,

SEQUENCE LISTING

```
<160> NUMBER OF SEQ ID NOS: 2

<210> SEQ ID NO 1
<211> LENGTH: 13
<212> TYPE: DNA
<213> ORGANISM: Artificial Sequence
<220> FEATURE:
<223> OTHER INFORMATION: Primer

<400> SEQUENCE: 1
ggtggacttt cgc                                                         13

<210> SEQ ID NO 2
<211> LENGTH: 20
<212> TYPE: RNA
<213> ORGANISM: Artificial Sequence
<220> FEATURE:
<223> OTHER INFORMATION: Template

<400> SEQUENCE: 2
acgacgugcg aaaguccacc                                                  20
```

[Chemical Formula 3B]

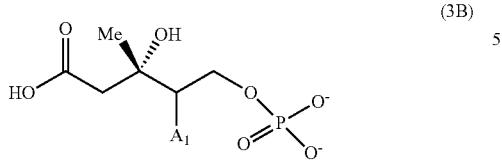

(3B)

wherein $A_1$ represents —$SR_1$, —S—S—$R_1$, —$SeR_1$, or —X where, X is a halogen selected from fluoro, chloro, bromo, and iodo; $R_1$ represents hydrogen, an alkyl group having 1 to 20 carbon atoms, an aryl group having 1 to 20 carbon atoms, or an alkenyl group having 1 to 20 carbon atoms, by phosphorylating the β-modified phosphoric acid compound precursor, and generating an active species represented by the following formula 3C by partially cleaving the β-modified phosphoric acid compound,

[Chemical Formula 3C]

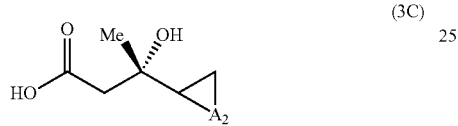

(3C)

wherein $A_2$ represents —S—, —$S^+(R_1)$—, —$S^+(S$—$R_1)$—, —$Se^+(R_1)$—, or —$X^+$—, where X means a halogen selected from fluoro, chloro, bromo, and iodo, and $R_1$ represents hydrogen, an alkyl group having 1 to 20 carbon atoms, an aryl group having 1 to 20 carbon atoms, or an alkenyl group having 1 to 20 carbon atoms.

5. The β-modified phosphoric acid compound precursor according to claim 1, wherein $A_1$ comprises —SH, —$SCH_3$, —S—$C_2H_5$, —S—$C_3H_7$, —S—SH, —S—S—$CH_3$, —S—S—$C_2H_5$, or —S—S—$C_3H_7$.

6. A β-modified phosphoric acid compound precursor, comprising
a structure represented by the following formula 4A,
[Chemical Formula 4A]

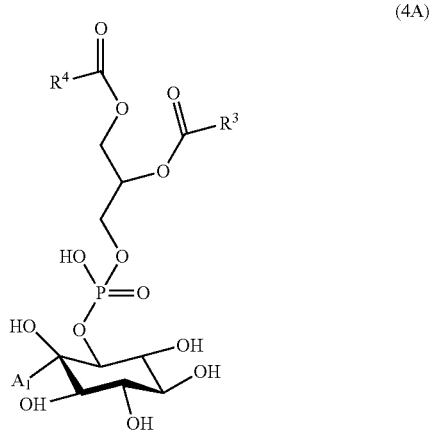

(4A)

wherein $A_1$ represents —$SR_1$, —S—S—$R_1$, —$SeR_1$, or —X, where X is a halogen selected from the group consisting of fluoro, chloro, bromo, and iodo; $R_1$ represents hydrogen, an alkyl group having 1 to 20 carbon atoms, an aryl group having 1 to 20 carbon atoms, or an alkenyl group having 1 to 20 carbon atoms; $R_3$ is an unsaturated fatty acid selected from the group consisting of arachidonic acid, linoleic acid, and linolenic acid; and $R_4$ is a saturated fatty acid selected from the group consisting of stearic acid, and palmitic acid.

7. A reaction inhibitor comprising the β-modified phosphoric acid compound precursor according to claim 6.

8. A pharmaceutical composition, comprising the reaction inhibitor according to claim 7.

9. The β-modified phosphoric acid compound precursor of claim 6, wherein $A_1$ comprises —SH, —$SCH_3$, —S—$C_2H_5$, —S—$C_3H_7$, —S—SH, —S—S—$CH_3$, —S—S—$C_2H_5$, or —S—S—$C_3H_7$.

10. A reaction inhibitor for a phosphorylation reaction, comprising a β-modified phosphoric acid compound precursor,
wherein the β-modified phosphoric acid compound precursor is a nucleoside derivative represented by the following formula 2A or a nucleic acid having the nucleoside derivative represented by the following formula 2A at the 3'-end thereof, and inhibits a reaction of a DNA polymerase,
[Chemical Formula 2A]

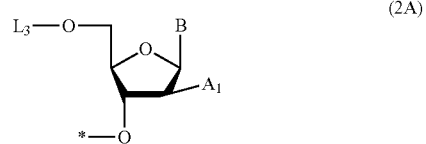

(2A)

wherein $A_1$ represents —$SR_1$, —S—S—$R_1$, —$SeR_1$, or —X, where X is a halogen selected from the group consisting of fluoro, chloro, bromo, and iodo; $R_1$ represents hydrogen, an alkyl group having 1 to 20 carbon atoms, an aryl group having 1 to 20 carbon atoms, or an alkenyl group having 1 to 20 carbon atoms; $L_3$ represents a monophosphate group, diphosphate group, or triphosphate group represented by the following formula 2D,
[Chemical Formula 2D]

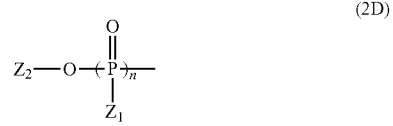

(2D)

where n is an integer of 1 to 3, $Z_1$ represents a hydroxyl group, or a methyl ester, ethyl ester, isopropyl ester, n-butyl ester, benzyl ester, or phenyl ester of glycine, alanine, valine, leucine, phenylalanine, tryptophan, methionine, or proline, $Z_2$ represents an alkyl group having 1 to 4 carbon atoms, a halogen, or a phenyl group, and when n is 2 or more, each $Z_1$ may be the same as or different from each other $Z_1$; and B represents a base selected from the group consisting of adeninyl, guaninyl, cytosinyl, thyminyl, uracilyl, N-methyladeninyl, N-benzoyladeninyl, 2-methylthioadeninyl, 2-aminoadeninyl, 7-methylguaninyl, N-isobutyrylguaninyl, 5-fluorocytosinyl, 5-bromocytosinyl, 5-methylcytosinyl, 4-N-methylcytosinyl, 4-N,N-dimethylcytosinyl, 5-fluorouracilyl, 5-bromouracilyl, 5-chlorouracilyl, and 5,6-dihydrouracilyl; and the symbol * represents a bond to be bonded to a phosphate group by phosphorylation, and defines bonding of hydrogen or a substituent before the phosphorylation, wherein the substituent is not a phosphate group.

11. A pharmaceutical composition, comprising the reaction inhibitor according to claim 10.

12. A method for inhibiting a phosphorylation reaction by the reaction inhibitor according to claim 10, comprising:
preparing a β-modified phosphoric acid compound precursor represented by formula 2A; and
generating a β-modified phosphoric acid compound represented by the following formula 2B,

[Chemical Formula 2B]

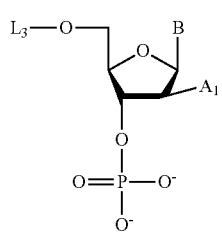

(2B)

wherein $A_1$ represents —$SR_1$, —S—S—$R_1$, —$SeR_1$, or —X where, X is a halogen selected from fluoro, chloro, bromo, and iodo; $R_1$ represents hydrogen, an alkyl group having 1 to 20 carbon atoms, an aryl group having 1 to 20 carbon atoms, or an alkenyl group having 1 to 20 carbon atoms; $L_3$ represents a monophosphate group, diphosphate group, or triphosphate group represented by the following formula 2D,

[Chemical Formula 2D]

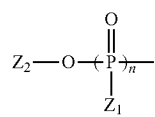

(2D)

where n is an integer of 1 to 3; $Z_1$ represents a hydroxyl group, or a methyl ester, ethyl ester, isopropyl ester, n-butyl ester, benzyl ester, or phenyl ester of glycine, alanine, valine, leucine, phenylalanine, tryptophan, methionine, or proline; $Z_2$ represents an alkyl group having 1 to 4 carbon atoms, a halogen, or a phenyl group; and when n is 2 or more, each $Z_1$ may be the same as or different from each other $Z_1$; and B represents a base selected from adeninyl, guaninyl, cytosinyl, thyminyl, uracilyl, N-methyladeninyl, N-benzoyladeninyl, 2-methylthioadeninyl, 2-aminoadeninyl, 7-methylguaninyl, N-isobutyrylguaninyl, 5-fluorocytosinyl, 5-bromocytosinyl, 5-methylcytosinyl, 4-N-methylcytosinyl, 4-N,N-dimethylcytosinyl, 5-fluorouracilyl, 5-bromouracilyl, 5-chlorouracilyl, or 5,6-dihydrouracilyl, by phosphorylating the β-modified phosphoric acid compound precursor, and generating an active species represented by the following formula 2C by partially cleaving the β-modified phosphoric acid compound,

[Chemical Formula 2C]

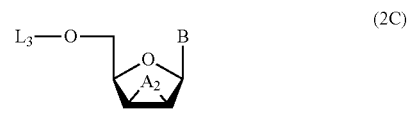

(2C)

wherein $A_2$ represents —S—, —$S^+(R_1)$—, —$S^+(S—R_1)$—, —$Se^+(R_1)$—, or —$X^+$—, where X is a halogen selected from the group consisting of fluoro, chloro, bromo, and iodo; $R_1$ represents hydrogen, an alkyl group having 1 to 20 carbon atoms, an aryl group having 1 to 20 carbon atoms, or an alkenyl group having 1 to 20 carbon atoms; $L_3$ represents a monophosphate group, diphosphate group, or triphosphate group represented by the following formula 2D,

[Chemical Formula 2D]

(2D)

where n is an integer of 1 to 3, $Z_1$ represents a hydroxyl group, or a methyl ester, ethyl ester, isopropyl ester, n-butyl ester, benzyl ester, or phenyl ester of glycine, alanine, valine, leucine, phenylalanine, tryptophan, methionine, or proline, $Z_2$ represents an alkyl group having 1 to 4 carbon atoms, a halogen, or a phenyl groups, and when n is two or more each $Z_1$ may be the same as or different from each other $Z_1$; and B represents a base selected from the group consisting of adeninyl, guaninyl, cytosinyl, thyminyl, uracilyl, N-methyladeninyl, N-benzoyladeninyl, 2-methylthioadeninyl, 2-aminoadeninyl, 7-methylguaninyl, N-isobutyrylguaninyl, 5-fluorocytosinyl, 5-bromocytosinyl, 5-methylcytosinyl, 4-N-methylcytosinyl, 4-N,N-dimethylcytosinyl, 5-fluorouracilyl, 5-bromouracilyl, 5-chlorouracilyl, and 5,6-dihydrouracilyl.

* * * * *

UNITED STATES PATENT AND TRADEMARK OFFICE
CERTIFICATE OF CORRECTION

PATENT NO. : 11,597,745 B2  
APPLICATION NO. : 16/977525  
DATED : March 7, 2023  
INVENTOR(S) : Hiroshi Abe et al.

Page 1 of 1

It is certified that error appears in the above-identified patent and that said Letters Patent is hereby corrected as shown below:

In the Claims

Column 54, Lines 9-16, Claim 1, delete " 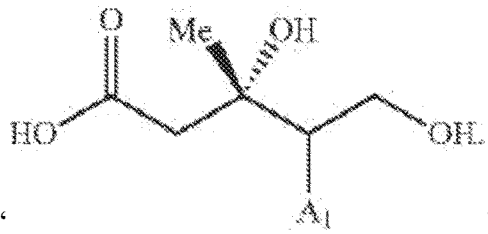 " and insert

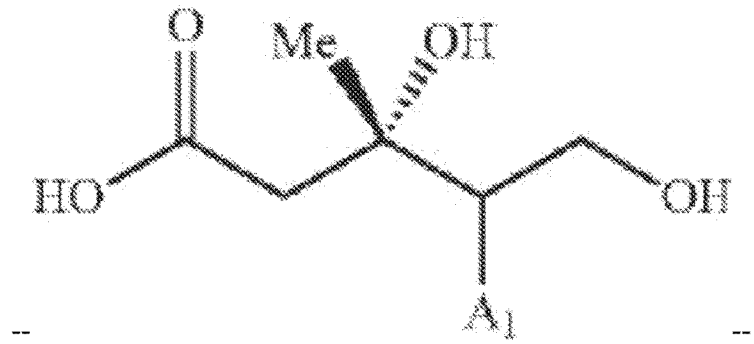

-- --

Signed and Sealed this  
Sixteenth Day of May, 2023

Katherine Kelly Vidal  
*Director of the United States Patent and Trademark Office*